US012636297B2

(12) United States Patent
Lomovskaya

(10) Patent No.: US 12,636,297 B2
(45) Date of Patent: May 26, 2026

(54) BORONIC ACID DERIVATIVES AND THERAPEUTIC USES THEREOF

(71) Applicant: Qpex Biopharma, Inc., San Diego, CA (US)

(72) Inventor: Olga Lomovskaya, Mountain View, CA (US)

(73) Assignee: QPEX BIOPHARMA, INC., San Diego, CA (US)

( * ) Notice: Subject to any disclaimer, the term of this patent is extended or adjusted under 35 U.S.C. 154(b) by 1020 days.

(21) Appl. No.: 17/619,752

(22) PCT Filed: Jun. 17, 2020

(86) PCT No.: PCT/US2020/038171
§ 371 (c)(1),
(2) Date: Dec. 16, 2021

(87) PCT Pub. No.: WO2020/257306
PCT Pub. Date: Dec. 24, 2020

(65) Prior Publication Data
US 2023/0144152 A1 May 11, 2023

Related U.S. Application Data

(60) Provisional application No. 62/863,752, filed on Jun. 19, 2019.

(51) Int. Cl.
*A61K 31/69* (2006.01)
*A61K 31/546* (2006.01)
*A61P 31/04* (2006.01)

(52) U.S. Cl.
CPC ............ *A61K 31/69* (2013.01); *A61K 31/546* (2013.01); *A61P 31/04* (2018.01)

(58) Field of Classification Search
CPC ........ A61K 31/69; A61K 31/546; A61P 31/04
See application file for complete search history.

(56) References Cited

U.S. PATENT DOCUMENTS

| | | | |
|---|---|---|---|
| 3,686,398 | A | 8/1972 | Kohn et al. |
| 4,194,047 | A | 3/1980 | Christensen et al. |
| 4,260,543 | A | 4/1981 | Miller |
| 4,353,807 | A | 10/1982 | Braid |
| 4,409,214 | A | 10/1983 | Takaya et al. |
| 4,812,561 | A | 3/1989 | Hamashima et al. |
| 4,822,786 | A | 4/1989 | Zama et al. |
| 4,933,443 | A | 6/1990 | Hamashima et al. |
| 5,442,100 | A | 8/1995 | Bjorkquiest et al. |
| 5,888,998 | A | 3/1999 | Maiti et al. |
| 6,184,363 | B1 | 2/2001 | Shoichet et al. |
| 6,218,380 | B1 | 4/2001 | Cole et al. |
| 6,586,615 | B1 | 7/2003 | Kettner et al. |
| 7,271,186 | B1 | 9/2007 | Shoichet et al. |
| 7,439,253 | B2 | 10/2008 | Lampilas et al. |
| 7,582,621 | B2 | 9/2009 | Baker et al. |
| 7,612,087 | B2 | 11/2009 | Aszodi et al. |
| 7,674,913 | B2 | 3/2010 | Campbell et al. |
| 7,825,139 | B2 | 11/2010 | Campbell et al. |
| 8,680,136 | B2 | 3/2014 | Hirst et al. |
| 9,012,491 | B2 | 4/2015 | Reddy et al. |
| 9,101,638 | B2 | 8/2015 | Reddy et al. |
| 9,132,140 | B2 | 9/2015 | Reddy et al. |
| 9,156,858 | B2 | 10/2015 | Reddy et al. |
| 9,241,947 | B2 | 1/2016 | Reddy et al. |
| 9,296,763 | B2 | 3/2016 | Hirst et al. |
| 9,511,142 | B2 | 12/2016 | Burns et al. |
| 9,642,869 | B2 | 5/2017 | Reddy et al. |
| 9,687,497 | B1 | 6/2017 | Bis et al. |
| 9,694,025 | B2 | 7/2017 | Hirst et al. |
| 10,004,758 | B2 | 6/2018 | Hirst et al. |
| 10,085,999 | B1 | 10/2018 | Gordon et al. |
| 10,206,937 | B2 | 2/2019 | Reddy et al. |
| 10,294,249 | B2 | 5/2019 | Hecker et al. |
| 10,570,159 | B2 | 2/2020 | Hecker et al. |
| 10,618,918 | B2 | 4/2020 | Hecker et al. |
| 10,662,205 | B2 | 5/2020 | Hecker et al. |
| 11,180,512 | B2 | 11/2021 | Hecker et al. |
| 11,286,270 | B2 | 3/2022 | Hecker et al. |
| 11,999,759 | B2 | 6/2024 | Hecker et al. |
| 12,016,868 | B2 | 6/2024 | Reddy et al. |
| 2004/0019203 | A1 | 1/2004 | Micetich et al. |
| 2004/0157826 | A1 | 8/2004 | Lampilas et al. |
| 2005/0020572 | A1 | 1/2005 | Aszodi et al. |

(Continued)

FOREIGN PATENT DOCUMENTS

| | | | |
|---|---|---|---|
| CN | 102320960 | A | 1/2012 |
| CN | 106397454 | A | 2/2017 |

(Continued)

OTHER PUBLICATIONS

Ito et al, J Antimicrob Chemother 2016; 71: 670-677 (Year: 2016).*
Serajuddin, Abu T.M., Advanced Drug Delivery Reviews 59 (2007) 603-616. (Year: 2007).*
Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.
Adediran et al., "A 'cephalosporin-like' cyclic depsipeptide: Synthesis and reaction with beta-lactam-recognizing enzymes", Bioorg Med Chem Lett. (1999) 9(3):341-346.
Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

(Continued)

*Primary Examiner* — Jared Barsky
*Assistant Examiner* — Janet L Coppins
(74) *Attorney, Agent, or Firm* — Knobbe, Martens, Olson & Bear, LLP

(57) ABSTRACT

Disclosed herein are antimicrobial compounds compositions, pharmaceutical compositions, the method of use and preparation thereof. Some embodiments relate to boronic acid derivatives and their use as therapeutic agents, for example, β-lactamase inhibitors (BLIs).

22 Claims, 2 Drawing Sheets

(56) References Cited

U.S. PATENT DOCUMENTS

| | | | |
|---|---|---|---|
| 2005/0070719 A1 | 3/2005 | Belyakov et al. | |
| 2006/0019116 A1 | 1/2006 | Conley et al. | |
| 2006/0178357 A1 | 8/2006 | Buynak et al. | |
| 2006/0210883 A1 | 9/2006 | Chen et al. | |
| 2009/0093423 A2 | 4/2009 | Udayampalayam et al. | |
| 2010/0056478 A1 | 3/2010 | Desarbre et al. | |
| 2010/0120715 A1 | 5/2010 | Burns et al. | |
| 2010/0256092 A1 | 10/2010 | Xia et al. | |
| 2010/0292185 A1 | 11/2010 | Burns et al. | |
| 2011/0288063 A1 | 11/2011 | Maiti et al. | |
| 2012/0040932 A1 | 2/2012 | Hirst et al. | |
| 2013/0316978 A1 | 11/2013 | Reddy et al. | |
| 2013/0331355 A1 | 12/2013 | Griffith et al. | |
| 2013/0345172 A1 | 12/2013 | Hirst et al. | |
| 2014/0194381 A1 | 7/2014 | Reddy et al. | |
| 2014/0194382 A1 | 7/2014 | Reddy et al. | |
| 2014/0194384 A1 | 7/2014 | Reddy et al. | |
| 2014/0194385 A1 | 7/2014 | Reddy et al. | |
| 2014/0194386 A1 | 7/2014 | Burns et al. | |
| 2014/0206648 A1 | 7/2014 | Reddy et al. | |
| 2014/0274954 A1 | 9/2014 | Chellappan et al. | |
| 2015/0119363 A1 | 4/2015 | Dudley et al. | |
| 2016/0220591 A1 | 8/2016 | Hirst et al. | |
| 2016/0339045 A1 | 11/2016 | Griffith et al. | |
| 2017/0057979 A1 | 3/2017 | Hecker et al. | |
| 2017/0088561 A1 | 3/2017 | Reddy et al. | |
| 2017/0136047 A1 | 5/2017 | Reddy et al. | |
| 2017/0173055 A1 | 6/2017 | Bis et al. | |
| 2018/0002351 A1* | 1/2018 | Hecker .................. | C07F 5/025 |
| 2018/0051041 A1 | 2/2018 | Hecker et al. | |
| 2018/0071325 A1 | 3/2018 | Hirst et al. | |
| 2018/0207183 A1 | 7/2018 | Hirst et al. | |
| 2018/0214465 A1 | 8/2018 | Hirst et al. | |
| 2019/0202832 A1 | 7/2019 | Basarab et al. | |
| 2021/0361682 A1 | 11/2021 | Reddy et al. | |
| 2022/0056055 A1 | 2/2022 | Hecker et al. | |
| 2023/0151029 A1 | 5/2023 | Reddy et al. | |
| 2024/0197750 A1 | 6/2024 | Griffith et al. | |
| 2024/0307422 A1 | 9/2024 | Reddy et al. | |
| 2024/0327426 A1 | 10/2024 | Hecker et al. | |
| 2025/0002508 A1 | 1/2025 | Hecker et al. | |
| 2025/0034175 A1 | 1/2025 | Hecker et al. | |

FOREIGN PATENT DOCUMENTS

| | | | |
|---|---|---|---|
| CN | 106397455 A | 2/2017 | |
| CN | 106397457 A | 2/2017 | |
| CN | 106420617 A | 2/2017 | |
| CN | 106420760 A | 2/2017 | |
| CN | 106432270 A | 2/2017 | |
| CN | 106432271 A | 2/2017 | |
| CN | 106432272 A | 2/2017 | |
| CN | 109293678 A | 2/2019 | |
| EP | 0069962 A1 | 1/1983 | |
| EP | 1550657 A1 | 7/2005 | |
| EP | 2508506 A1 | 10/2012 | |
| EP | 2406233 B1 | 11/2013 | |
| FR | 2573070 A1 | 5/1986 | |
| JP | 2003-229277 | 8/2003 | |
| JP | 2004-291253 | 10/2004 | |
| WO | WO 1987/05297 | 9/1987 | |
| WO | WO 1989/10961 | 11/1989 | |
| WO | WO 1998/56392 A1 | 12/1998 | |
| WO | WO 2000/035904 A1 | 6/2000 | |
| WO | WO 2000/035905 A1 | 6/2000 | |
| WO | WO 2001/023374 A1 | 4/2001 | |
| WO | WO 2001/030149 | 5/2001 | |
| WO | WO 2002/022137 A1 | 3/2002 | |
| WO | WO 2002/083884 | 10/2002 | |
| WO | WO 2003/070714 | 8/2003 | |
| WO | WO 2004/039859 | 5/2004 | |
| WO | WO 2004/058679 A2 | 7/2004 | |
| WO | WO 2004/064755 A2 | 8/2004 | |
| WO | WO 2005/033090 | 4/2005 | |
| WO | WO 2005/035532 A1 | 4/2005 | |
| WO | WO 2005/087700 | 9/2005 | |
| WO | WO 2006/052733 A1 | 5/2006 | |
| WO | WO 2006/091771 | 8/2006 | |
| WO | WO 2007/058602 A2 | 5/2007 | |
| WO | WO 2007/065288 A2 | 6/2007 | |
| WO | WO 2007/095638 | 8/2007 | |
| WO | WO 2008/039420 A2 | 4/2008 | |
| WO | WO 2008/116813 A1 | 10/2008 | |
| WO | WO 2009/046098 A1 | 4/2009 | |
| WO | WO 2009/064413 A1 | 5/2009 | |
| WO | WO 2009/064414 A1 | 5/2009 | |
| WO | WO 2009/091856 A1 | 7/2009 | |
| WO | WO 2009/117540 A1 | 9/2009 | |
| WO | WO 2009/139834 A1 | 11/2009 | |
| WO | WO 2009/140309 A2 | 11/2009 | |
| WO | WO 2010/056827 A1 | 5/2010 | |
| WO | WO 2010/075286 A1 | 7/2010 | |
| WO | WO 2010/097675 A1 | 9/2010 | |
| WO | WO 2010/130708 A1 | 11/2010 | |
| WO | WO 2010/144338 A1 | 12/2010 | |
| WO | WO 2011/017125 A1 | 2/2011 | |
| WO | WO 2011/103686 A1 | 9/2011 | |
| WO | WO 2011/123502 A1 | 10/2011 | |
| WO | WO 2011/154953 | 12/2011 | |
| WO | WO 2012/021455 A1 | 2/2012 | |
| WO | WO 2012/058065 A1 | 5/2012 | |
| WO | WO 2012/067664 A1 | 5/2012 | |
| WO | WO 2012/106995 A1 | 8/2012 | |
| WO | WO 2012/136383 A1 | 10/2012 | |
| WO | WO 2013/033461 A1 | 3/2013 | |
| WO | WO 2013/053372 A1 | 4/2013 | |
| WO | WO 2013/056163 A1 | 4/2013 | |
| WO | WO 2013/092979 A1 | 6/2013 | |
| WO | WO 2013/104774 A1 | 7/2013 | |
| WO | WO 2013/104897 A1 | 7/2013 | |
| WO | WO 2013/122888 A2 | 8/2013 | |
| WO | WO 2013/184845 A1 | 12/2013 | |
| WO | WO 2014/089365 A1 | 6/2014 | |
| WO | WO 2014/107535 A1 | 7/2014 | |
| WO | WO 2014/107536 A1 | 7/2014 | |
| WO | WO 2014/110442 A1 | 7/2014 | |
| WO | WO 2014/144380 A1 | 9/2014 | |
| WO | WO 2014/151958 A1 | 9/2014 | |
| WO | WO 2015/171430 A1 | 11/2015 | |
| WO | WO 2015/179308 A1 | 11/2015 | |
| WO | WO-2015171398 A1 * | 11/2015 | ........... A61K 31/397 |
| WO | WO 2015/191907 A1 | 12/2015 | |
| WO | WO 2016/003929 A1 | 1/2016 | |
| WO | WO 2016/065282 A1 | 4/2016 | |
| WO | WO 2016/116892 A1 | 7/2016 | |
| WO | WO 2016/149393 A1 | 9/2016 | |
| WO | WO 2017/100537 A1 | 6/2017 | |
| WO | WO 2018/005662 A1 | 1/2018 | |
| WO | WO 2018/013870 A1 | 1/2018 | |
| WO | WO 2019/075084 A1 | 4/2019 | |
| WO | WO 2019/093450 A1 | 5/2019 | |
| WO | WO 2020/112542 A1 | 6/2020 | |
| WO | WO 2021/041616 A1 | 3/2021 | |
| WO | WO 2021/188700 A1 | 9/2021 | |

OTHER PUBLICATIONS

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Allen et al., "Ansel's Pharmaceutical Dosage Forms and Drug Delivery Systems", 8th Edition (2004) TOC only.

Ambrose et al., Pharmacokinetics-pharmacodynamics of antimicrobial therapy: it's not just for mice anymore. Clin Infect Dis. (2007) 44: 79-86.

Ambrose et al., "Pharmacokinetics-pharmacodynamics of CB-618 in combination with cefepime, ceftazidime, ceftolozane and meropenem: the pharmacological basis for a stand-alone beta-lactamase inhibitor", Antimicrob Agents Chemother. (Nov. 2017) 61(12): e00630-17; 7 pages.

American Chemical Society. STN Chemical Database Registry RN: 1226917; Jun. 2010; 2 pages.

(56) References Cited

OTHER PUBLICATIONS

Arya et al., "Advances in asymmetric enolate methodology", Tetrahedron (2000) 56:917-947.
Austad et al. "Development of a multi kilogram-scale, tandem cyclopropanation ring-expansion reaction en route to hedgehog antagonist IPI-926", Org Process Res Dev., (2016) 20(4):786-798; Supporting Information, 70 pages.
Babic et al., "What's new in antibiotic resistance? Focus on beta-lactamases", Drug Res Updates (2006) 9:142-156.
Balbach et al., "Pharmaceutical evaluation of early development candidates 'the 100 mg-approach'", Int'l J Pharma. May 4, 2004;275: 1-12.
Bassetti et al., "New antibiotics for bad bugs: where are we?", Ann Clin Microbiol Antimicrob. (2013) 12:22-36.
Becker, Daniel E., "Antimicrobial Drugs", Anesth Prog (2013) 60:111-123.
Beenen et al., "Asymmetric copper-catalyzed synthesis of alpha-amino boronate esters from N-tert-butanesulfinyl aldimines", J Am Chem Soc. (2008) 130(22):6910-6911.
Berkhout et al., "Pharmacodynamics of Ceftazidime and Avibactam in Neutropenic Mice with Thigh or Lung Infection", Antimicrob Agents Chemother. (2015) 60 (1): 368-375.
Bhavani et al., Pharmacokinetic-Pharmacodynamic (PK_PD) basis for CLSI carbapenem (CARB) susceptibility breakpoint changes. abstr Abstracts of Papers, 50th Interscience Conference on Antimicrobial Agents and Chemotherapy, Sep. 12-15, 2010; #A1-1382, Boston, MA; 3 pages.
Biedrzycki et al., "Derivatives of tetrahedral boronic acids", J. Organomet. Chem. (1992) 431:255-270.
Bilello et al., "Effect of 2',3'-8 didehydro-3'-deoxythymidine in an in vitro hollow-fiber pharmacodynamic model system correlates with results of dose-ranging clinical studies", Antimicrob Agents Chemother. (1994) 38(6): 1386-1391.
Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Bowker et al., Comparative pharmacodynamics of meropenem using an in-vitro model to simulate once, twice and three times daily dosing in humans. J Antimicrob Chemother (1998) 42: 461-467.
Brabez et al., "Design, synthesis, and biological studies of efficient multivalent melanotropin ligands: tools toward melanoma diagnosis and treatment", J Med Chem. (2011) 54(20):7375-7384.
Braisted et al., "Discovery of a potent small molecule IL-2 inhibitor through fragment assembly", J Am Chem Soc., (2003) 125(13): 3714-3715; Supporting Information, 42 pages.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Buesking et al., "Asymmetric Synthesis of Protected alpha-Amino Boronic Acid Derivatives with an Air- and Moisture-stable Cu(II) Catalyst", J Org Chem. (Mar. 2014) 79(8): 3671-3677.
Bulik et al., "Comparison of the activity of a human simulated, high-dose, prolonged infusion of meropenem against Klebsiella pneumoniae producing the KPC carbapenemase versus that against Pseudomonas aeruginosa in an in vitro pharmacodynamic model", Antimicrob Agents Chemother (2010) 54(2): 804-810.
Bundgaard H. [Ed.], "Design of Prodrugs", Elsevier (1985); TOC, 2 pages.
Bush et al., "Minireview: Updated Functional Classification of beta-Lactamases," Antimicrob Agents Chemo. (2010) 54(3):969-976.
CAS Registry No. 2005:329437 CAPLUS; "Product subclass 28: Vinylboranes", Vaultier et al., (2004); XP-002764965; 1 page.
CAS Registry Nos. 69190-59/60 (2-(bis(phenylthio)methyl)-4,4,5,5-tetramethyl-1,3,2-dioxaborolane) and 69190-60-9 (2-(bis(phenylthio)methyl)-1,3,2-dioxaborinane) Scheme 18 (2015); 2 pages.
CAS Registry No. 105892-95-3 Boronic acid [1-(phenylsulfonyl)heptyl]-, dimethyl ester (2015); 2 pages.
CAS Registry No. 831209-98-4 6H-Dibenz[c,e][1,2]oxaborin, 6a, 10a-dihydro-6-hydroxy; Entered STN: Feb. 15, 2005; 1 page.
CAS Registry No. 831210-03-8 6H-Dibenz[c,e][1,2]oxaborin, 2,4-dibromo-6a, 10a-dihydro-6-hydroxy; Feb. 15, 2005; 1 page.
CAS Registry No. 2114651-20-4; "7-Benzofurancarboxylic acid", Aurora Fine Chemicals; Aug. 16, 2017; 1 page.
CAS Registry No. 1780853-40-8; "7-Benzofurancarboxylic acid", Aurora Fine Chemicals; Jun. 15, 2015; 1 page.
CAS Registry No. 1427326-65-5; "7-Benzofurancarboxylic acid", Ellanova Laboratories; Apr. 5, 2013; 1 page.
CAS Registry No. 1344904-36-4; "7-Benzofurancarboxylic acid", Asiba Pharmatech, Inc.; Nov. 13, 2011; 1 page.
CAS Registry No. 1890373-92-8; "Benzoic acid", Aurora Fine Chemicals; Apr. 15, 2016; 1 page.
Chandrasekhar et al., "The first Corey-Chaykovsky epoxidation and cyclopropanation in ionic liquids", Tetrahedron Letts. (2003) 44:3629-3630.
Charette et al., "Palladium-catalyzed Suzuki-type cross-couplings of iodocyclopropanes with boronic acids: Synthesis of trans-1,2-dicyclopropyl alkenes", J Org Chem. (1996) 61(25): 8718-8719; Supporting Information, 52 pages.
Cheng et al., "Inhibitors of hepatitis C virus polymerase: Synthesis and characterization of novel 2-oxy-6-fluoro-N-((S)-1-hydroxy-3-phenylpropan-2-yl)-benzamides", Bioorg Med Chem Ltts. (2010) 20:2119-2124.
Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.
Chemicalland21.com. "Meglumine", Jun. 7, 2011. Downloaded from </www.chemicalland21.com/lifescience/phar/N-METHYL-D-GLUCAMINE.htm>; 2 pages.
Chinchilla et al., "Recent advances in Sonogashira reactions", Chem Soc Rev., (2011) 40: 5084-5121.
Clark et al., "Concise synthesis of the C-1—C-12 fragment of amphidinolides T1-T5", Org Biomol Chem. (2011) 9(13): 4823-4830.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically; Approved Standard—9th Edition", CLSI (Jan. 2012) M07-A9 32(2): 88 pages.
Clinical Trial NCT02168946, "A Phase 3, Multi-Center, Randomized, Open-Label Study of Carbavance (Meropenem/RPX7009) Versus Best Available Therapy in Subjects with Selected Serious Infecations Due to Carbapenem-Resistant Enterobacteriaceae", 6. Oct. 2014; retrieved online from URL:https://clinicaltrials.gov/archive/NCT02168946/20140_10_06.
Conte et al., "Intrapulmonary pharmacokinetics and pharmacodynamics of meropenem", Int J Antimicrob Agents (Dec. 2005) 26(6):449-456.
Coppa et al., "A Facile, Convenient and Selective Homolytic Carbamolylation of Heteroaromatic Bases", Heterocycles (1993) 36(12):2687-2696.
Cornella et al., "Ni-catalyzed stereoselective arylation of inert C—O bonds at low temperatures". Org Lett. (2013) 15(24):6298-6301 with Supporting Information in 50 pages.
Coutts et al., "Two Efficient Methods for the Cleavage of Pinanediol Boronate Esters Yielding The Free Boronic Acids", Tetrahedron Lett. (1994) 35(29):5109-5112.

(56) References Cited

OTHER PUBLICATIONS

Craig WA., "Pharmacokinetic/pharmacodynamic parameters: rationale for antibacterial dosing of mice and men", Clin Infect Dis. (1998) 26(1): 1-10.
Cunha, "Meropenem in elderly and renally impaired patients", Int'l J Antimicro Agents (1998) 10: 107-117.
Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.
Darses et al., "Potassium Organotrifluoroborates: New Perspectives in organic Synthesis", Chem Rev. (2008) 108:288-325.
Davoli et al., "Enantioselective total synthesis of (−)-microcarpalide", Tetrahedron (2005) 61:4427-4436.
De Meijere A. [Ed], Science of Synthesis—vol. 24; "Three Carbon-Heteroatom Bonds: Ketene Acetals and Yne-X Compounds", TOC 46 pages.
Di Gioia et al., "Optically Pure N-Hydroxy-O-triisopropylsilyl-alpha-L-amino Acid Methyl Esters from AICI3-Assisted Ring Opening of Chiral Oxaziridines by Nitrogen Containing Nucleophiles", J Org Chem. (2005) 70(25):10494-10501.
Dörwald F.Z., Side Reactions in Organic Synthesis—A guide to Successful Synthesis Design, Wiley-VCH Verlag Gmbh & Co. KGaA, Weinheim, Germany (2005); Preface in 4 pages.
Drawz et al., "Three Decades of beta-Lactamase Inhibitors", Clin Microbiol Reviews (Jan. 2010) 23(1):160-201.
Drusano et al., Meropenem: clinical response in relation to in vitro susceptibility. Clin Microbiol Infect. (2000) 6: 185-194.
Dunetz et al., "Large-scale applications of amide coupling reagents for the synthesis of pharmaceuticals", Org Process Res Develop. (2016) 20(2): 140-177.
Eggen et al., "Total synthesis of cryptophycin-24 (Arenastatin A) amenable to structural modifications in the C16 side chain", J Org Chem. (2000) 65(23): 7792-7799; and Supporting documents, 22 pages.
Eidam et al., "Design, synthesis, crystal structures and antimicrobial activity of sulfonamide boronic acids as beta-lactamase inhibitors", J Med Chem. (2010) 53(21):7852-7863.
Eissenstat et al., "Aminoalkylindoles: Structure-Activity Relationships of Novel Cannabinoid Mimetics", J Med Chem. (1995) 38(16):3094-3105.
El Nezhawy et al., "Synthesis and antioxidant activity of some thiazolidin-4-one derivatives", Springer; Chemical Monthly/Monatshefte für Chemie (2009) 140(5):531-539.
Endo et al., "Chemoselective Suzuki coupling of diborylmethane for facile synthesis of benzylboronates", Org Lett. (2011) 13(13):3368-3371.
Fan, et al. (2009): STN International HCAPLUS database, Columbus (OH), accession No. 2009: 425839; 6 pages.
Farquhar et al., "Intensely potent doxorubicin analogues: structure—activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Giroux, A., "Synthesis of benzylic boronates via palladium-catalyzed cross-coupling reaction of bis(pinacolato)diboron with benzylic halides", Tetrahedron Lett. (2003) 44:233-235.
Goodman et al., [Eds.], "The Pharmacological Basis of Therapeutics", 8th. Edition, Pergamon Press (1990); TOC, 8 pages.
Gorovoy et al., "Boron-Containing Peptidomimetics—A Novel Class of Selective Anti-tubercular Drugs", Chem Biol Drug Des. (Jan. 2013) 81(3):408-413.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Graham et al., "D is for Drugs", Chemistry & Industry, Mar. 19, 2013, pp. 28-30, Downloaded from http://www.concertpharma.com/wp-content/uploads/2014/12/ChemistryIndustry-0313.pdf; 3 pages.
Greene, et al., "Greene's Protective Groups in Organic Synthesis", 4th Edition, (2007); pp. 774, 785 & 787.
Gunanathan et al., "Ruthenium catalyzed hydroboration of terminal alkynes to Z vinylboronates", J Am Chem Soc. (2012) 134(35): 14349-14352; Supporting Information, 32 pages.
Hall D.G., [Ed], Boronic Acids [vol. 2]: Preparations and applications in Organic Synthesis, Medicine and Materials, Wiley-VCH, Weinheim, 2nd Edition (2011); TOC.
Hama et al., "Palladium-Catalyzed alpha-Arylation of Zinc Enolates of Esters: Reaction Conditions and Substrate Scope", J Org Chem. (2013) 78(17): 8250-8266.
Hartung et al., "Highly Z-selective and Enantioselective Ring Opening/Cross Metathesis Catalyzed by Resolved Stereogenic-At-Ru Complex", J Am Chem Soc. (Jul. 2013) 135(28): 10183-10185.
He et al., "Ligand-promoted borylation of C(sp3)—H bonds with palladium(II) catalysts", Angew Chem Int Ed., (2016) 55(2): 785-789.
Hecker et al., "Discovery of a Cyclic Boronic Acid beta-Lactamase Inhibitor (RPX7009) with Utility vs Class A Serine Carbapenemases", J Med Chem. (Mar. 2015) 58:3682-3692.
Hecker et al., "Discovery of Cyclic Boronic Acid QPX7728, an Ultrabroad-Spectrum Inhibitor of Serine and Metallo-β-lactamases", J Med Chem. (Mar. 2020) 63: 7491-7507.
Higuchi et al., [Eds.] "Pro-drugs as Novel Drug Delivery Systems", ACS Sumposium Series 14 (1975); TOC, 3 pages.
Höpfl et al., "Dynamic NMR and X-ray diffraction study of (N—B)-diphenyl(2-aminoethoxy) borane derivatives of ephedrines and pseudoephedrines". J Organomet Chem. (1997) 544(2):175-188.
Hoveyda A., "Evolution of catalytic stereoselective olefin metathesis: From ancillary transformation to purveyor of stereochemical identity", J Org Chem. (Jun. 2014) 79(11): 4763-4792.
Hu et al., "Ag(I)-catalyzed C—H borylation of terminal alkynes", Tetrahedron (2014) 70: 5815-5819.
Imanishi et al., "Discovery of a Novel Series of Biphenyl Benzoic Acid Derivatives as Potent andSelective Human beta3-Adrenergic Receptor Agonists with Good Oral Bioavailability. Part I", J Med Chem. (2008) 51(6):1925-1944.
Inglis et al., "Observations on the Deprotection of Pinanediol and Pinacol Boronate Esters via Fluorinated Intermediates", J Org Chem. (2010) 75(2):468-471; Supporting Information, S 1-S-76.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ishiyama et al., "Palladium(0)-catalyzed cross-coupling reaction of alkoxydiboron with haloarenes: A direct procedure for arylboronic esters", J Org Chem. (1995) 60(23): 7508-7510; Supporting Information, 35 pages.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]- boronates from (alpha-Haloalkyl)boronates", Org Chem. (1996) 61(22):7951-7954.
Jagannathan et al., "Synthesis of Boronic Acid Analogues of alpha-Amino Acids by Introducing Side Chains as Electrophiles", J Org Chem. (2001) 66(19):6375-6380.
Jang et al., Copper-catalyzed trans-hydroboration of terminal aryl alkynes: Stereodivergent synthesis of alkenylboron compounds. Org Letts. (2016) 18(6): 1390-1393; Supporting Information in 37 pages.
Jarrett et al., "Nickel(II) bis(phosphine) complexes". Inorg Chem. (1991) 30(9):2098-2104 with Supporting Information in 7 pages.
Jiang et al., "A Practical Synthesis of Cefcapene Pivoxil", Synthesis (2012) 44:207-214.
Johnson et al., "A drug targeting motif for glycosidase inhibitors: An iminosugar-boronate shows unexpectedly selective beta-galactosidase inhibition", Tetrahed Lttrs. (2002) 43(49):8905-8908.
Jordan V.C., "Tamoxifen: A most unlikely pioneering medicine", Drug Discovery (2003) 2:205-213.

(56) References Cited

OTHER PUBLICATIONS

Kabalka et al., "Synthesis of a series of bornonated unnatural cyclic amino acids as potential boron neutron capture therapy agents", Appl Organomet Chem. (2008) 22(9):516-522.
Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", Chem Letts. (1993) 22(5):845-848.
Kawamorita et al., "Synthesis of Primary and Secondary Alkylboronates through Site-Selective C(sp3)—H Activation with Silica-supported Monophosphine-Ir Catalysts", J Am Chem Soc. (2013) 135(8):2947-2950.
Kikuchi et al., "Comparison of the Pharmacodynamics of Biapenem in Bronchial Epithelial Lining Fluid in Healthy Volunteers Given Half-Hour and Three-Hour Intravenous Infusions", Antimicrob Agents Chemother. (Sep. 2009) 53(7):2799-2803.
Kint et al., "New-found fundamentals of bacterial persistence", Trends Microbiol. (2012) 20(12):577-585.
Kinuta et al., "Rhodium-catalyzed borylation of aryl 2-pyridyl ethers through cleavage of the carbon-oxygen bond: borylative removal of the directing group". J Am Chem Soc. (2015) 137(4):1593-1600 with Supporting Information in 198 pages.
Kondo et al., Ruthenium-Catalyzed Monoalkenylation of Aromatic Ketones by Cleavage of Carbon-Heteroatom Bonds with Unconventional Chemoselectivity. Angew Chem Int Ed Engl. (2015) 54(32):9293-9297 with Supporting Information in 95 pages.
Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.
Kotha et al., "Recent applications of the suzuki-miyaura cross-coupling reaction in organic synthesis", Tetrahedron (2002) 58:9633-9695.
Kuang et al., "Convenient and stereoselctive synthesis of (Z)-1-bromo-1-alkenes by microwave-induced reaction", Tetrahedron Letts. (2001) 42(23): 3893-3896.
Kumar et al., "Synthesis of intermediates for the lactone moiety of mevinic acids via tellurium chemistry", J. Org. Chem., (1994) 59(17):4760-4764.
Kumar et al., "Development of Practical Methodologies for the Synthesis of Functionalized Benzoboroxoles", Tetrahedron Lett. (Aug. 25, 2010) 51(34):4482-4485.
Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.
Kuti et al., "Use of Monte Carlo simulation to design an optimized pharmacodynamic dosing strategy for meropenem", J Clin Pharmacol. (Oct. 2003) 43(10): 1116-1123 with Erratum (2005); 1 page.
Laitar et al., "Catalytic diboration of aldehydes via insertion into the copper-boron bond", J Am Chem Soc. (2006) 128(34):11036-11037.
Lapuebla et al., "Activity of Meropenem Combined with RPX7009, a Novel beta-Lactamase Inhibitor, against Gram-Negative Clinical Isolates in New York City", Antimicrob Agents Chemother. (Aug. 2015) 59(8):4856-4860.
Larock R. [Ed.] Comprehensive Organic Transformations, VCH Publishers 1989; TOC, 11 pages.
Lebel et al., "Boc-protected amines via a mild and efficient one-pot Curtius rearrangement", Org Letts. (2005) 7(19): 4107-4110.
Lee et al., "Vicinal Diboronates in High Enantiomeric Purity through Tandem Site-Selective NHC—Cu-Catalyzed Boron-Copper Additions to Terminal Alkynes", J Am Chem Soc. (Dec. 2009) 131(51):18234-18235.
Lee et al., "Comparison of 30-min and 3-h infusion regimens for imipenem/cilastatin and for meropenem evaluated by Monte Carlo simulation", Diagn Microbiol Infect Dis. (2010) 68: 251-258.
Li et al., "Population Pharmacokinetic Analysis and Dosing Regimen Optimization of Meropenem in Adult Patients", J Clin Pharmacol. (2006) 46(10): 1171-1178.
Li et al., "Novel macrocyclic Hcv NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.
Li et al., "Stereoselective total synthesis of etnangien and etnangien methyl ester", J Org Chem. (2010) 75(8):2429-2444.
Liang et al., "The Efficient Copper(I) (Hexabenzyl)tren Catalyst and Dendritic Analogues for Green"Click" Reactions between Azides and Alkynes in Organic Solvent and in Water: Positive Dendritic Effects and Monometallic Mechanism", Advance Syn Catal. (2011) 353(18): 3434-3450.
Lieberman H.A. [Ed] Pharmaceutical Dosage Forms—Tablets; Marcel Dekker, Inc. (1989) 2nd Ed; TOC; 7 pages.
Lima et al., "Bioisosterism: A Useful Strategy for Molecular Modification and Drug Design", Curr Med Chem. (2005) 12:23-49.
Lin et al., "Pharmacokinetics and dose proportionality of ceftibuten in men", Antimicro Agents Chemother. (1995) 39(2): 359-361.
Lin et al., "Enantioselective syn and anti homocrotylation of aldehydes: Application to the formal synthesis of spongidepsin", J Am Chem Soc. (2015) 137(40): 13176-13182; Supporting Information, 177 pages.
Liu et al., "Selective Protein tyrosine phosphatase 1B inhibitors: Targeting the second phosphotyrosine binding site with non-carboxylic acid-containing ligands", J Med Chem. (2003) 46(16):3437-3440; Supporting Information, 38 pages.
Liu et al., "Application of Stereoselective Ether Transfer to the Synthesis of Isotactic Polyethers", J Org Chem. (2010) 75(12):3953-3957.
Livermore et al., "Activities of NXL104 combinations with Ceftazidime and Aztreonam against Carbapenemase-producing Enterobacteriaceae", Antimicr Agents Chemother. (2011) 55(1):390-394.
Livermore et al., "Activity of biapenem (RPX2003) combined with the boronate beta-lactamaseinhibitor RPX7009 against carbapenem-resistant Enterobacteriaceae", J Antimicrob Chemother. (Aug. 2013) 68(8):1825-1831.
Lodise et al., "Penetration of meropenem into epithelial lining fluid of patients with ventilator-associated pneumonia", Antimicrob Agents Chemother. (Apr. 2011) 55(4):1606-1610.
Louie et al., Impact of meropenem in combination with tobramycin in a murine model of Pseudomonas aeruginosa pneumonia. Antimicrob Agents Chemother (2013) 57: 2788-2792.
Luithle et al., "Synthesis of enantiomerically pure cis-cyclopropylboronic esters", Eur J Org Chem. (2000) 14: 2557-2562.
MacVane et al., Characterizing in vivo pharmacodynamics of carbapenems against Acinetobacter baumannii in a Murine thigh infection model to support breakpoint determinations. Antimicrob Agents Chemother (2014) 58: 599-601.
Maguire B. A., Inhibition of Bacterial Ribosome Assembly: a Suitable Drug Target? Microbiol Mol Biol Rev. (2009) 73(1):22-35.
Malfertheiner et al., "Current concepts in the management of Helicobacter pylori infection: the Maastricht III Consensus Report", Gut (2007) 56(6):772-781.
Matteson et al., "Iodomethaneboronic Esters and Aminomethaneboronic Esters", J Organomet. Chem. (1979) 170:259-264.
Matteson et al., "A Directed Chiral Synthesis of Amino Acids from Boronic Esters", Tetrahedron Lett. (1987) 28(39):4499-4502.
Matteson, D.S., "Asymmetric Synthesis with Boronic Esters", Acc Chem Res. (1988) 21(8):294-300.
Matteson, "Boronic esters in stereodirected synthesis", Tetrahedron (1989) 45(7): 1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Matteson et al., "(Alkoxyalkyl)boronic Ester Intermediates for Asymmetric Synthesis", Organometallics (1996) 15:152-163.
Matteson, "Alpha-Halo Baronic Esters in Asymmetric Synthesis", Tetrahedron (1998) 54(36):10555-10607.

(56) References Cited

OTHER PUBLICATIONS

Matteson et al., "Glass-Catalyzed Conversion of Boronic Esters of Asymmetric Diols to Diol Sulfites and Amine Complexes of Boron Halides", Oranometallics (2001) 20(13):2920-2923 & supporting Information (9 pages).
Matteson et al., "Cesium Alkyltrifluoroborates from Asymmetric Boronic Esters", Synlett (Jul. 2006) 20:3501-3503.
Matteson et al., "Synthesis of a (Beta-acetamido-alpha-acetoxyethyl) boronic ester via azido boronic esters", J Organomet Chem. (2008) 693:2258-2262.
Matteson, "Boronic Esters in Asymmetric Synthesis", J Org Chem. (Oct. 2013) 78(20): 10009-10023.
Mcomie J.R.W. [Ed], Protective Groups in Organic Chemistry, Plenum Press, London & New York (1973); TOC, 3 pages.
Meanwell, "Synopsis of some recent tactical application of bioisosteres in drug design", J. Med. Chem. (2011) 54:2529-2591.
McSharry et al., "Prediction of the pharmacodynamically linked variable of oseltamivir carboxylate for influenza A virus using an in vitro hollow-fiber infection model system", Antimicrob Agents Chemother (2009) 53(6): 2375-2381.
Mendoza et al., "Bis(phenylthio) methaneboronic Esters as Sources of Carbanions and Ketene Thioacetals", J Org Chem. (1979) 44(8):1352-1354.
Micalizio et al., "A Boronic Ester Annulation Strategy for Diversity-Oriented Organic Synthesis", Angew Chem Int Ed Engl. (2002) 41(1):152-154.
Miriagou et al., "Acquired carbapenemases in Gram-negative bacterial pathogens: detection and surveillance issues", Clin Microbiol Infect. (Feb. 2010) 16(2):112-122.
Mkhalid et al., "C—H activation for the construction of C—B bonds", Chem Rev. (2010) 110(2): 890-931.
Molander et al., "Highly stereoselective synthesis of cis-alkenyl pinacolboronates and potassium cis-alkenyltrifluoroborates via a hydroboration/protodeboronation approach", J Org Chem. (2008) 73(17): 6841-6844.
Montalbetti et al., "Amide bond formation and peptide coupling", Tetrahedron (2005) 61:10827-10852.
Montefour et al., "Acinetobacter baumannii: an emerging multidrug-resistant pathogen in critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Mori et al., "Synthesis of 1,3-dienes from alkynes and ethylene: Acetic acid 2-methylene-3-phenethylbut-3-enyl ester", Org Synth. (2005) 81: 1-13.
Morrill et al., "Treatment Options for Carbapenem-Resistant Enterobacteriaceae Infections", Open Forum Infectious Diseases [OFID] Apr. 2015; 15 pages.
Munar et al., "Drug Dosing Adjustments in Patients with Chronic Kidney Disease", Am Fam Physician (May 2007) 75(1): 1487-1496.
Ness et al., "Structure-based design guides the improved efficacy of deacylation transition state analogue inhibitors of TEM-1 beta-Lactamase", Biochemistry (2000) 39(18):5312-5321.
Nicasio et al., "Pharmacokinetics-Pharmacodynamics of Tazobactam in Combination with Piperacillin in an In Vitro Infection Model", Antimicrob Agents Chemother. (2016) 60: 2075-2080. doi: 10.1128/AAC.02747-15.
Nicolau DP., "Pharmacokinetic and pharmacodynamic properties of meropenem", Clin Infect Dis. (2008) 47 Suppl 1: S32-S40.
Noguchi et al., "Boron-masking strategy for the selective synthesis of oligoarenes via iterative Suzuki-Miyaura coupling", J Am Chem Soc. (2007) 129(4): 758-759; Supporting Information, 46 pages.
Nordmann et al., How to Detect NDM-1 Producers, J. Clin. Micro. (2011) 49:718-721.
O'Brien et al., "Enantioselective Synthesis of Boron-Substituted Quaternary Carbons by NHC—Cu-Catalyzed Boronate Conjugate Additions to Unsaturated Carboxylic Esters, Ketones or Thioesters." J Am Chem Soc. (2010) 132(31): 10630-10633.
Overman et al., "Organic Synthesis—Working with Hazardous Chemicals", Org Synth. (1990) 68: 182; 5 pages.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Paquette L.A. [Ed.] Encyclopedia of Reagents for Organic Synthesis, vol. 1; J. Wiley & Sons (1995); Cover Only.
Patani et al., "Bioisosterism: A Rational Approach in Drug Design", Chem Rev. (1996) 96:3147-3176.
Paterson et al., "Extended-Spectrum beta-Lactamases: a Clinical Update", Clin Microbiol Rev. (2005) 18(4):657-686.
Pellissier, H., "Recent developments in asymmetric cyclopropanation", Tetrahedron (2008) 64(30-31): 7041-7095.
Perez et al., "Why are we afraid of Acinetobacter baumannii?", Expert Rev Anti Infect Ther. (2008) 6(3): 269-71.
Pietruszka et al., "Enantiomerically pure cyclopropylamines from cyclopropylboronic esters", Eur J Org Chem. (2009) 34: 5998-6008.
Pine et al., "Resonance vs. Tautomerism" in Organic Chemistry; McGraw-Hill, New York 4th Ed. (1980), pp. 218-219.
Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34):11825-11827.
Queenan et al., "Carbapenemases: the Versatile β-Lactamases", Clin Microbiol Rev. (Jun. 2007) 20(3):440-458.
Rehm et al., "*Staphylococcus aureus*: Methicillin-susceptible *S. aureus* to Methicillin-resistant *S. aureus* and Vancomycin-resistant *S. aureus*", Clin Inf Diseases. (2010) 51(S2):S176-S182.
Reich et al., "Organoselenium chemistry. Alkylation of acid, ester, amide, and ketone enolates with bromomethyl benzyl selenide and sulfide. Preparation of selenocysteine derivatives", J Organ Chem. (1986) 51(15): 2981-2988.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Rhoads et al., "The Claisen and Cope Rearrangements", Organic Reactions Chapter 1 (1975) 22: 1-166.
Robak et al., "Synthesis and applications of tert-butanesulfinamide", Chem Rev. (2010) 110(6):3600-3740.
Roche, E.B. (Ed.), Bioreversible Carriers in Drug Design: Theory and Application. New York: Pergamon Press (1987); pp. 14-21.
Rodriguez-Martinez et al., "VIM-19, a Metallo-beta-lactamase with increased Carbapenemase Activity from *Escherichia coli* and Klebsiella pneumoniae", Antimicro Agents Chemother. (2010) 54(1):471-476.
Rosen et al., "Nickel-catalyzed cross-couplings involving carbon-oxygen bonds". Chem Rev. (2011) 111(3):1346-1416.
Rubino et al., "Phase 1 Study of the Safety, Tolerability, and Pharmacokinetics of Vaborbactam and Meropenem Alone and in Combination following Single and Multiple Doses in Healthy Adult Subjects", Antimicrob Agents Chemother. (Apr. 2018) 62(4): E02228-17; 12 pages.
Sabet et al., "In Vivo Efficacy of Carbavance (Meropenem/RPX7009) Against KPC-producing Enterobacteriaceae", Abstracts of the 54th Interscience Conference on Antimicrobial Agents and Chemotherapy (Sep. 5-9, 2014) F-958; 3 pages.
Sabet et al., "Activity of Simulated Human Dosage Regimens of Meropenem and Vaborbactamagainst Carbapenem-Resistant Enterobacteriaceae in an In Vitro Hollow-Fiber Model", Antimicrob Agents Chemother (2017) 62. pii: e01969-17. doi: 10.1128/AAC.01969-17.
Sabet et al., "Activity of Meropenem-Vaborbactam in Mouse Models of Infection Due to KPC-Producing Carbapenem-Resistant Enterobacteriaceae", Antimicrob Agents Chemother. (2017) 62:1 10e01446-379 17.
Saito et al., "Nickel-catalyzed boron insertion into the C2—O bond of benzofurans". J Am Chem Soc. (2016)., 138(47), 15315-15318 with Supporting Information in 103 pages.
Sawant et al., "Synthesis of the C1—C13 Fragment of Biselyngbyaside", Synlett (2011) 20: 3002-3004.

(56) References Cited

OTHER PUBLICATIONS

Sawyer et al., "Physical properties and synthetic utility of a-alkoxyorganolithium species as studied through ligand selectivity in tin-lithium exchange", J. Am. Chem. Soc. (1988) 110:842-853.
Schwarzer et al., "Combined theoretical and experimental studies of nickel-catalyzed cross-coupling of methoxyarenes with arylboronic esters via C—O bond cleavage". J Am Chem Soc. (2017) 139(30):10347-10358 with Suppl. Information in 255 pages.
Scriven et al., "Azides: Their preparation and synthetic uses", Chem Rev. (1988) 88(2): 297-368.
Selander et al., "Palladium-catalyzed allylic C—OH functionalization for efficient synthesis of functionalized allylsilanes", J Am Chem Soc. (2011) 133(3):409-411.
Shaffer, Robyn Kroop, "The Challenge of Antibiotic-Resistant *Staphylococcus*: Lessons from Hospital Nurseries in the mid-20th Century", Yale J Biol Med. (2013) 86:261-270.
Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.
Singer et al., "Catalytic, enantioselective acetate aldol additions to alpha-, beta-ynals: Preparation of optically active propargylic alcohols", Tetrahedron (1998) 54(25): 7025-7032.
Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.
Singh et al., "Confronting the challenges of discovery of novel antibacterial agents", Bioorg Med Chem Lett. (2014) 24(16):3683-3689.
Singhal et al., "Drug polymorphism and dosage form design: A practical perspective", Adv Drug Deliv Rev. Feb. 23, 2004;56(3): 335-347.
Sliwka et al., "Synthetic Sulfur Carotenoids II: Optically Active Carotenoid Thiols", Tetrahedron: Asymmetry (1993) 4(3):361-368.
Solladié et al., "First Stereocontrolled Synthesis of the (3S,5R,7R,10R,11R)-C1-C13 Fragment of Nystatin A(1)", J Org Chem. (1999) 64(15):5447-5452.
Souto et al., "Synthesis and biological characterization of the histone deacetylase inhibitor largazole and c7-modified analogues", J. Med. Chem. (2010) 53(12):4654-4667.
Spiegel et al., "CP-263, 114 synthetic studies. Construction of an isotwistane ring system via rhodium carbenoid C—H insertion", Tetrahedron (2002) 58:6545-6554.
Stivala et al., "Highly enantioselective direct alkylation of arylacetic acids with chiral lithium amides as traceless auxiliaries." J Am Chem Soc., (2011)133(31): 11936-11939.
Sumida et al., "Boron-selective biaryl coupling approach to versatile dibenzoxaborins and application to concise synthesis of defucogilvocarcin M", Org Ltt. (2014/12) 16(23):6240-6243.
Sun et al., "A method for the deprotection of alkylpinacolyl boronate esters", J Org Chem. (2011) 76(9):3571-3575; Supporting Information, 8 pages.
Sun et al., "Programmed Synthesis of a Contiguous Stereotriad Motif by Triple Stereospecific Reagent-controlled Homologation", Org Lttr. (Jul. 2013) 15(17):4500-4503.
Tam et al., "Optimization of meropenem minimum concentration/MIC ratio to suppress in vitro resistance of Pseudomonas aeruginosa", Antimicrob Agents Chemother. (2005) 49(12): 4920-4927.
Tang et al., "New Chiral Phosphorus Ligands for Enantioselective Hydrogenation." Chem Rev. (2003) 103: 3029-3070.
Teo et al., "Efficient and highly aldehyde selective Wacker oxidation", Org Lett. (2012) 14(13):3237-3239.
Theuretzbacher et al., "Update on antibacterial and antifungal drugs—can we master the resistance crisis?", Curr Opin Pharmacol. (2011) 11:429-432.
Tobisu et al., "Nickel-catalyzed alkylative cross-coupling of anisoles with Grignard reagents via C—O bond activation". J Am Chem Soc. (2016) 138(47):6711 and Suppl. Information in 105 pages.
Ty et al., "Synthesis and biological evaluation of enantiomerically pure cyclopropyl analogues of combretastatin A4". Bioorg Med Chem (2013) 21:1357-1366.
U.S. Department of Health and Human Resources, "Antibiotic Resistance Threats in the United States, 2013"; 114 pages.
Valters et al., "Ring-Chain Tautomerism", Plenum Press, New York and London, Softcover reprint of the hardcover 1st Ed. 1985, Chapter 1, 23 pages.
VanScoy et al., "Pharmacokinetics-pharmacodynamics of tazobactam in 386 combination with ceftolozane in an in vitro infection model", Antimicrob Agents Chemother. (2013) 57: 2809-2814. doi: 10.1128/AAC.02513-12.
Vasil'ev et al., (1977): STN International HCAPLUS database, Columbus (OH), accession No. 1977: 72730; 1 page.
Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.
Voituriez et al., "Preparation of a storable zinc carbenoid species and its application in cyclopropanation, chain extension, and [2,3]-sigmatropic rearrangement reactions", J Org Chem. (2010) 75(4): 1244-1250; Supporting Information, 20 pages.
Waley, Stephen G., "A quick method for the determination of inhibition constants", Biochem J. (1982) 205(3):631-633.
Walker et al., "Pharmacodynamic activities of meropenem in an animal infection model", (1994), Abstracts of Papers #A91, 34th Interscience Conference on Antimicrobial Agents and Chemotherapy, Orlando , FL., 5 pages.
Walsh et al., "Metallo-beta-Lactamases: the Quiet before the Storm?", Clin Microbiol Rev. (2005) 18(2):306-325.
Wang et al., "Recognition and resistance in TEM beta-lactamase", Biochemistry (2003) 42(28):8434-8444.
Webb et al., "Metal catalysed hydroboration of vinyl sulfides, sulfoxides, sulfones, and sulfonates", J Mol Cat A: Chem. (2007) 275:91-100.
Wenkert et al., "Nickel-induced conversion of carbon-oxygen into carbon-carbon bonds. One-step transformations of enol ethers into olefins and aryl ethers into biaryls".(1979) 101(8):2246-2247.
Wilson D.N., "The A-Z of bacterial translation inhibitors", Crit Rev Biochem Mol Biolog. (2009) 44(6):393-433.
Wohlrab et al., "Total synthesis of plusbacin A3: a depsipeptide antibiotic active against vancomycin-resistant bacteria", J. Am. Chem. Soc. (2007) 129:4175-4177.
Wong et al., "A chemoselective Reformatsky-Negishi approach to α-haloaryl esters", Tetrahedron (2014) 70(7): 1508-1515.
Xia et al., "Synthesis and SAR of novel benzoxaboroles as a new class of beta-lactamase inhibitors", Bioorg Med Chem Lett. (2011) 21:2533-2536.
Xie et al., "Group-assisted purification (GAP) chemistry for the synthesis of Velcade via asymmetric borylation of N-phosphinylimines", Beilstein J Org Chem (Mar. 2014) 10:746-751.
Yamamoto et al., "Iridium-catalyzed hydroboration of alkenes with pinacolborane", Tetrahedron (2004) 60:10695-10700.
Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.
Yuen et al., "Deprotection of pinacolyl boronate esters via hydrolysis of intermediate potassium trifluoroborates", Tetrahed Lttr. (2005) 46(46):7899-7903.
Zhang et al., "Catalytic boracarboxylation of alkynes with diborane and carbon dioxide by an N-heterocyclic carbene copper catalyst." J Am Chem Soc. (2012) 134(35): 14314-14317.
Zhu et al., "Design, preparation, x-ray crystal structure, and reactivity of o-alkoxyphenyliodoniumbis(methoxycarbonyl)methanide, a highly soluble carbene precursor", Org Lett. (2012) 14(12): 3170-3173; Supporting Information, 76 pages.
Banker G.S. et al. [Eds.], Modern Pharmaceutics, 4th Edition; Marcel Dekker, Inc. (2002); Chapters 9 and 10, 98 pages.
CAS Registry No. 2170834-63-4; Benzo[e]cycloprop[c][1,2]oxaborin-4-carboxylic acid, 5-fluoro-1,1a,2,7b-tetrahydro-2-hydroxy-, (1aR,7bS); Jan. 23, 2018; 1 Page.

(56) References Cited

OTHER PUBLICATIONS

CAS Registry No. 2170848-99-2; 'Borate(2), [3-[(1 S2R)-cyclopropyl-Kc2]-6-fluoro-2-(hydroxy-$_{K}$O)benzoato(3-)]dihydroxy-, sodium (1:2), (t-4)'; Jan. 24, 2018; ? Page.-carboxylic acid, 5-fluoro-1,1a,2,7b-tetrahydro-2-hydroxy-, (1aR,7bS)'; Jan. 23, 2018; 1 Page.

Hong et al., "Ceftolozane/tazobactam: A Novel Antipseudomonal Cephalosporin and β-lactamase-inhibitor Combination", Infect Drug Resist. (2013) 6: 215-223.

Monogue et al., "Efficacy of Humanized Exposures of Cefiderocol (S-649266) against a Diverse Population of Gram-negative Bacteria in a Murine Thigh Infection Model", Antimicrob Agents Chemother. (2017) 61(11): e01022-17 in 10 pages.

Nema et al., "Excipients and Their Role in Approved Injectable Products: Current Usage and Future Directions", PDA J Pharm Sci Technol. (2011) 65(3):287-332.

Powell et al., "Compendium of excipients for parenteral formulations", PDA J Pharm Sci Technol. (1998) 52(5):238-311.

International Search Report and Written Opinion dated Jul. 30, 2020 for International Application No. PCT/US2020/038171, filed Jun. 17, 2020.

Cahill et al., Cyclic Boronates Inhibit All Classes of β-Lactamases. Antimicro Age Chemother. Apr. 2017;61(4): e02260-16.

CAS Registry No. 1964:447952 CAPLUS; "Arylboronic acids. VII. Some reactions of o-formylbenzenebornic acid", Tschampel et al. J Org Chem. Aug. 1964;29(8): 2168-2172; Abstract.

CAS Registry No. 2006320-60-9; "3,4-dihydro-2-hydroxy-2H-1,2-Oxaborino[6,5-c]pyridine- 8-carboxylic acid", CAS, Oct. 5, 2016; 1 page.

Pettersson et al., Discovery of cyclopropyl chromane-derived pyridopyrazine-1, 6-dione γ-secretase modulators with robust central efficacy. MedChemComm. 2017;8(4): 730-743.

Roy et al., "Polymorph discrimination using low wavenumber Raman spectroscopy". Org Process Res Dev. Jul. 19, 2013;17(7):976-980.

Zhanel et al., "Cefiderocol: A siderophore cephalosporin with activity against carbapenem-resistant and multidrug-resistant gram-negative bacilli", Drugs. Feb. 28, 2019;79: 271-289.

Hosokawa, R., "Conductivity Measurement / General Tests", The Japanese Pharmacopoeia, Sixteenth Edition, Mar. 2011, pp. 64-68, 2070.

Lomovskaya et al., "Spectrum of beta-lactamase inhibition by the cyclic boronate QPX7728, an ultrabroad-spectrum beta-lactamase inhibitor of serine and metallo-beta-lactamases: enhancement of activity of multiple antibiotics against isogenic strains expressing single beta-lactamases". Antimicro Agents Chemother.. May 21, 2020;64(6): 10-128.

Stewart et al., "Oral cephalosporin and [beta]-lactamase inhibitor combinations for ESBL-producing Enterobacteriaceae urinary tract infections". J Antimicro Chemother. Sep. 1, 2020;75(9):2384-2393.

Byrn et al., "Pharmaceutical Solids: A Strategic Approach to Regulatory Considerations". Pharma Res. Jul. 1995;12(7):945-954.

Grant, D.J.W., "Theory and Origin of Polymorphism". in Polymorphism in Pharmaceutical Solids, Harry G. Brittain [Ed], Drugs Pharma Sciences 2nd Ed., (Dec. 31, 1999), Chapter 1; pp. 1-10.

Guillory J.K., "Generation of Polymorphs, Hydrates, Solvates, and Amorphous Solids" in Polymorphism in Pharmaceutical Solids, Harry G. Brittain [Ed], Drugs Pharma Sciences 2nd Ed., (Dec. 31, 1999), Chapter 5; pp. 183-226. (3-part doc).

Gupta et al., "Salts of Therapeutic Agents: Chemical, Physiocochemical, and Biological Considerations". Molecules. Jul. 14, 2018;23(7):1719 in 15 pages.

Lomovskaya et al., Impact of Intrinsic resistance mechanisms on potency of QPX7728, a new ultrabroad-spectrum beta-lactamase inhibitor of serine and metallo-beta-lactamases in Enterobacteriaceae, Pseudomonas aeruginosa, and Acinetobacter baumannil. Antimicrobial agents and chemotherapy. May 21, 2020;64(6):e00552-20 in 11 pages.

Shah et al., "Salt Formation" in Pharmaceutical Dosage Forms: Tablets; Larry L. Augsburger et al. [Eds.]; 3rd edition, vol. 2, chapter 2, p. 62-66, Dec. 31, 2008.

European Extended Search Report dated Aug. 11, 2025 for Application No. 25175312.5, filed Nov. 11, 2020.

* cited by examiner

A

MER, meropenem; TOL, ceftolozane; SUL, sulbactam; C1, Compound 1; CP, carbapenemase

B

KPC (N=1), NDM (N=4), OXAs (23/40/72/239, N=95), OXA-23 (N=75)

Compound 1 tested at 8 μg/mL
No MBL (KPC=162, OXA-48-like=150, non-CP-CRE=52); MBL (NDM=132, VIM=10, IMP=3)

BORONIC ACID DERIVATIVES AND THERAPEUTIC USES THEREOF

BACKGROUND

Field

The present application relates to the fields of chemistry and medicine. More particularly, the present application relates to boronic acid antimicrobial compounds, compositions, their preparation, and their use as therapeutic agents.

Description of the Related Art

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactam antibiotics. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as *Acinetobacter baumannii* has become an emerging multidrug-resistant threat. *A. baumannii* strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K. et al., *Crit. Care Nurse* 2008, 28, 15; Perez, F. et al., *Expert Rev. Anti Infect. Ther.* 2008, 6, 269; Bou, G.; Martinez-Beltran, J., *Antimicrob. Agents Chemother.* 2000, 40, 428. 2006, 50, 2280; Bou, G. et al., *J. Antimicrob. Agents Chemother.* 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in *Klebsiella pneumoniae* but now also reported in other *Enterobacteriaceae, Pseudomonas aeruginosa* and *Acinetobacter baumannii*. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

The zinc-dependent class B metallo-β-lactamases are represented mainly by the VIM, IMP, and NDM types. IMP and VIM-producing *K. pneumonia* were first observed in 1990s in Japan and 2001 in Southern Europe, respectively. IMP-positive strains remain frequent in Japan and have also caused hospital outbreaks in China and Australia. However, dissemination of IMP-producing *Enterobacteriaceae* in the rest of the word appears to be somewhat limited. VIM-producing enterobacteria can be frequently isolated in Mediterranean countries, reaching epidemic proportions in Greece. Isolation of VIM-producing strains remains low in Northern Europe and in the United States. In stark contrast, a characteristic of NDM-producing *K. pneumonia* isolates has been their rapid dissemination from their epicenter, the Indian subcontinent, to Western Europe, North America, Australia and Far East. Moreover, NDM genes have spread rapidly to various species other than *K. pneumonia.*

The plasmid-expressed class D carbapenemases belong to OXA-48 type. OXA-48 producing *K. pneumonia* was first detected in Turkey, in 2001. The Middle East and North Africa remain the main centers of infection. However, recent isolation of OXA-48-type producing organisms in India, Senegal and Argentina suggest the possibility of a global expansion. Isolation of OXA-48 in bacteria other than *K. pneumonia* underlines the spreading potential of OXA-48.

Treatment of strains producing any of these carbapenemases with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in *Pseudomonas aeruginosa*. Efflux pump over expression combined with hyperproduction of the ampC β-lactamase can also result in resistance to a carbapenem such as meropenem.

Thus, there is a need for improved therapies using β-lactamase inhibitors (BLIs).

SUMMARY

Some embodiments described herein relate to pharmaceutical compositions comprising a therapeutically effective amount of a compound, or a pharmaceutically acceptable salt thereof, having the structure:

(1)

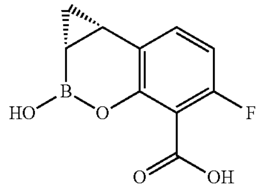

or

-continued (1-a)

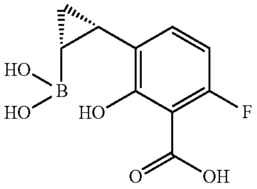

and a pharmaceutically acceptable excipient; and further comprising an additional medicament, wherein the additional medicament may be ceftolozane or sulbactam.

Other embodiments described herein relate to pharmaceutical compositions comprising a therapeutically effective amount of a compound, or a pharmaceutically acceptable salt thereof, having the structure:

(1)

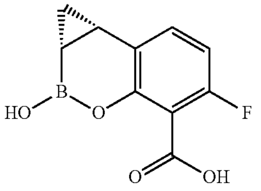

or (1-a)

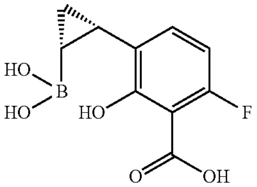

and a pharmaceutically acceptable excipient; and further comprising an additional medicament, wherein the additional medicament may be cefiderocol.

In some embodiments, the pharmaceutically acceptable salt may be an alkaline metal salt or an ammonium salt. In some embodiments, the sodium salt may be

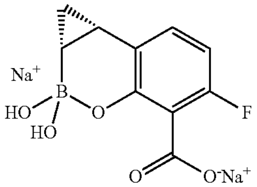

or

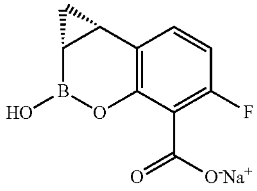

.

In other embodiments, the sodium salt may be

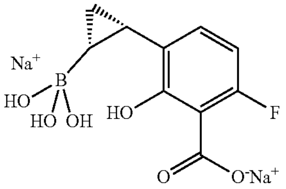

or

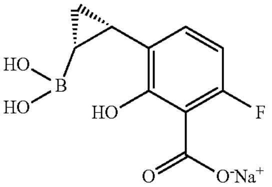

.

Some embodiments described herein relate to method of treating a bacterial infection, comprising administering to a subject a pharmaceutical composition comprising a compound, or a pharmaceutically acceptable salt thereof, having the structure:

(1)

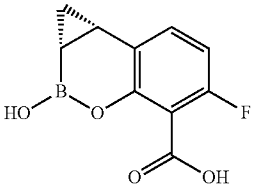

or (1-a)

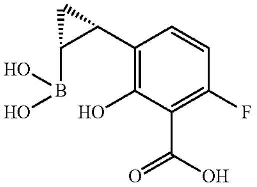

in combination with ceftolozane or sulbactam.

Some embodiments described herein relate to method of treating a bacterial infection, comprising administering to a subject a pharmaceutical composition comprising a compound, or a pharmaceutically acceptable salt thereof, having the structure:

(1)

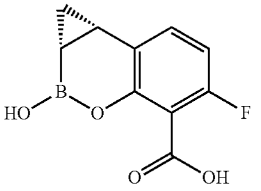

or (1-a)

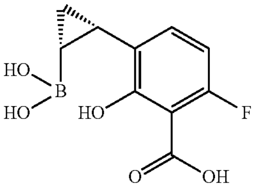

in combination with cefiderocol.

In some embodiments, the infection may comprise a bacteria selected from the group consisting of *Pseudomonas acidovorans, Pseudomonas alcaligenes, Pseudomonas putida, Burkholderia cepacia, Aeromonas hydrophilia, Francisella tularensis, Morganella morganii, Proteus mirabilis, Proteus vulgaris, Providencia alcalifaciens, Providencia rettgeri, Providencia stuartii, Acinetobacter baumannii, Bordetella pertussis, Bordetella para pertussis, Bordetella bronchiseptica, Haemophilus ducreyi, Pasteurella multocida, Pasteurella haemolytica, Branhamella catarrhalis, Borrelia burgdorferi, Kingella, Gardnerella vaginalis, Bacteroides distasonis, Bacteroides* 3452A homology group, *Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, and *Staphylococcus saccharolyticus.*

In other embodiments, the infection may comprise a bacteria selected from the group consisting of *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, and *Bacteroides splanchnicus.*

In some specific embodiments, the infection may comprise the bacteria *Pseudomonas aeruginosa*. In other specific embodiments, the infection may comprise the bacteria *Acinetobacter baumannii.*

Some embodiments described herein relate to method of treating a bacterial infection, comprising administering to a subject in need thereof a compound or a pharmaceutically acceptable salt thereof, having the structure:

(1)

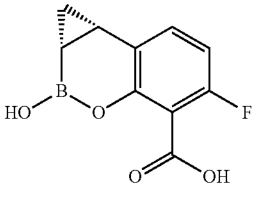

or

-continued (1-a)

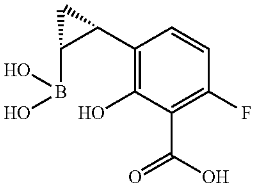

and an additional medicament, wherein the additional medicament may be ceftolozane or sulbactam.

In some embodiments, the compound and additional medicament may be administered simultaneously. In other embodiments, the compound and additional medicament may be administered sequentially.

In some specific embodiments, the infection may comprise the bacteria *Pseudomonas aeruginosa*. In other specific embodiments, the infection may comprise the bacteria *Acinetobacter baumannii.*

DETAILED DESCRIPTION OF EMBODIMENTS

Compound 1

Figure 1:
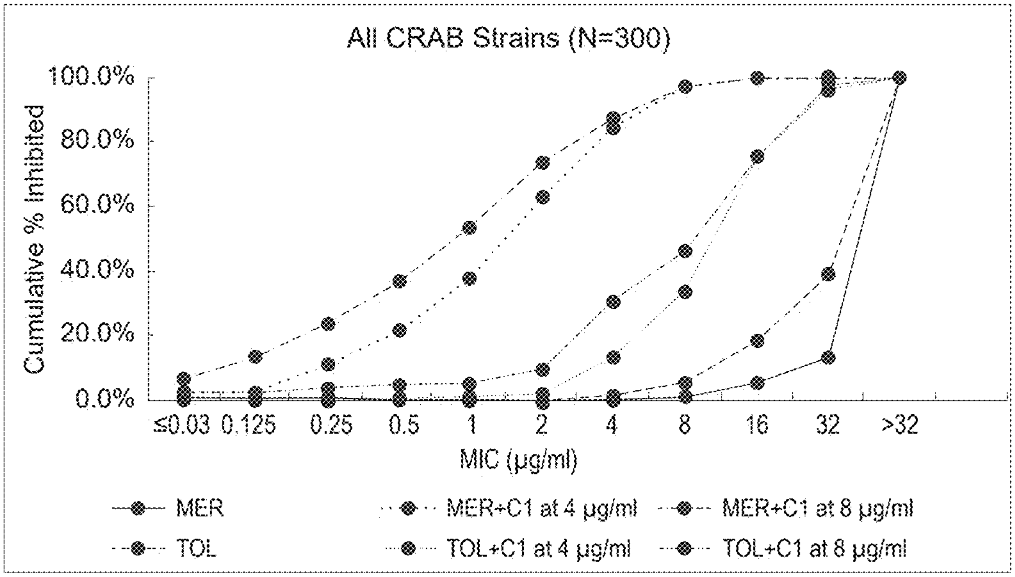
FIG. 1A shows the minimum inhibitory concentration distribution of Compound 1 combinations against Carbapenem-Resistant *Acinetobacter baumannii.*
FIG. 1B shows the minimum inhibitory concentration distribution of Compound 1 combinations against Carbapenem-Resistant *Acinetobacter baumannii* having a defined Carbapenemase.
Figure 1:
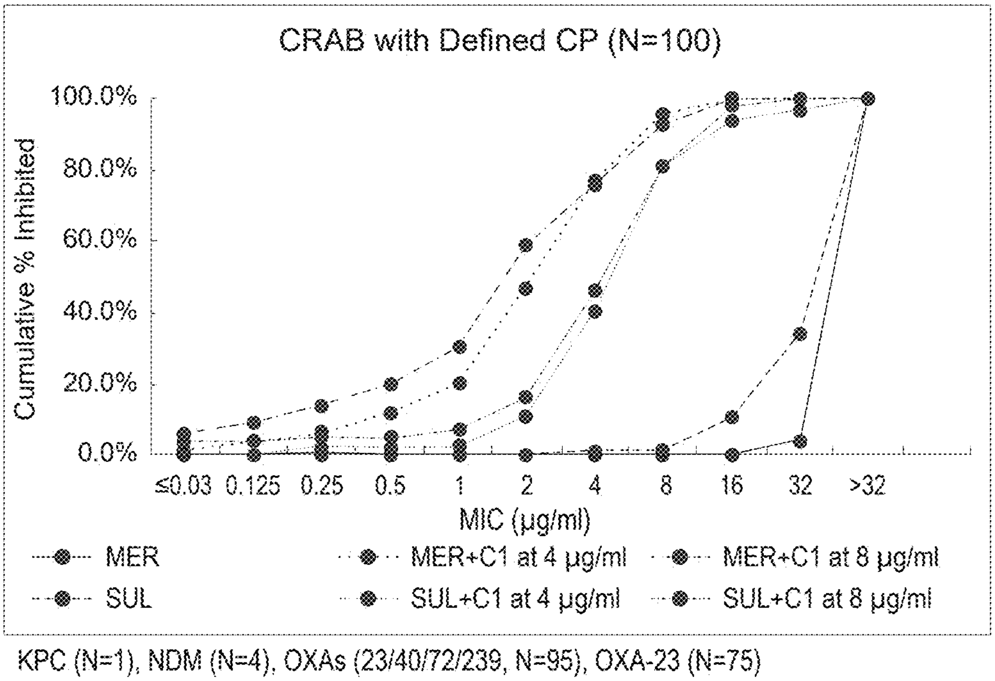

Some embodiments provided herein include Compound 1, (1)

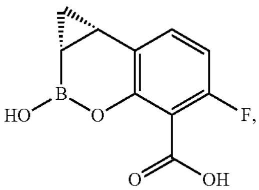

, or a pharmaceutically acceptable salt thereof, which contains a boronic acid moiety. Compound 1 can act as an antimicrobial agent and/or as a potentiator of antimicrobial agents.

In some embodiments, the pharmaceutically acceptable salts are selected from alkaline metal salts or ammonium salts. In one embodiment, the pharmaceutically acceptable salts are sodium salts, including disodium salts.

In some embodiments, due to the facile exchange of boron esters, Compound 1 described herein may convert to or exist in equilibrium with alternate forms. Accordingly, in some embodiments, Compound 1 described herein may exist in combination with one or more of these forms. For example, as shown below, Compound 1 disclosed herein may exist in a cyclic boronate monoester with the structure of Compound 1-a depending on the medium. Exemplary equilibrium equation between Compound 1 and Compound 1-a in aqueous medium is demonstrated below:

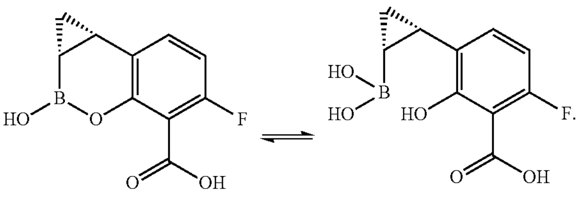

1 1-a

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms “a,” “an” and “the” include plural referents unless the context clearly dictates otherwise. The use of “or” or “and” means “and/or” unless stated otherwise. Furthermore, use of the term “including” as well as other forms, such as “include”, “includes,” and “included,” is not limiting. As used in this specification, whether in a transitional phrase or in the body of the claim, the terms “comprise(s)” and “comprising” are to be interpreted as having an open-ended meaning. That is, the terms are to be interpreted synonymously with the phrases “having at least” or “including at least.” When used in the context of a process, the term “comprising” means that the process includes at least the recited steps, but may include additional steps. When used in the context of a compound, composition, or device, the term “comprising” means that the compound, composition, or device includes at least the recited features or components, but may also include additional features or components.

“Subject” as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

The term “mammal” is used in its usual biological sense. Thus, it specifically includes, but is not limited to, primates, including simians (chimpanzees, apes, monkeys) and humans, cattle, horses, sheep, goats, swine, rabbits, dogs, cats, rodents, rats, mice guinea pigs, or the like.

The term “pharmaceutically acceptable carrier” or “pharmaceutically acceptable excipient” includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman’s: The Pharmacological Basis of Therapeutics, 8th Ed., Pergamon Press.

A therapeutic effect relieves, to some extent, one or more of the symptoms of a disease or condition, and includes curing a disease or condition. “Curing” means that the symptoms of a disease or condition are eliminated; however, certain long-term or permanent effects may exist even after a cure is obtained (such as extensive tissue damage).

“Treat,” “treatment,” or “treating,” as used herein refers to administering a compound or pharmaceutical composition to a subject for prophylactic and/or therapeutic purposes. The term “prophylactic treatment” refers to treating a subject who does not yet exhibit symptoms of a disease or condition, but who is susceptible to, or otherwise at risk of, a particular disease or condition, whereby the treatment reduces the likelihood that the patient will develop the disease or condition. The term “therapeutic treatment” refers to administering treatment to a subject already suffering from a disease or condition.

Compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that the structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

“Solvate” refers to the compound formed by the interaction of a solvent and a compound described herein, a metabolite, or salt thereof. Suitable solvates are pharmaceutically acceptable solvates including hydrates.

The term “pharmaceutically acceptable salt” refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

Some examples of pharmaceutically acceptable base addition salts of Compound 1 or 1-a disclosed herein have the structure of Compoud 1' or Compound 1-a':

1'

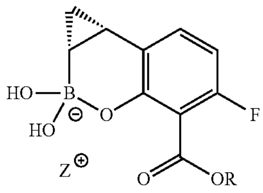

or 1-a'

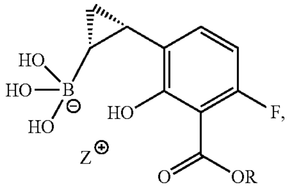

wherein each of $Z^{\oplus}$ and R may be independently selected from an alkali metal cation or an ammodium cation ($NH_4^+$).

Some examples of pharmaceutically acceptable base addition salts of Compound 1 or 1-a disclosed herein have the structure of Compound 1" or Compound 1-a":

1"

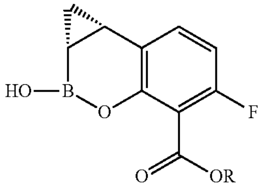

or 1-a"

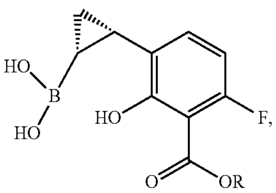

wherein each R may be independently selected from an alkali metal cation or an ammodium cation ($NH_4^+$).

In some embodiments, the salt of Compound 1 has the structure

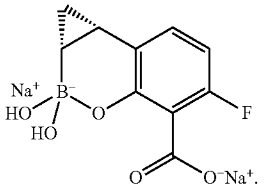

In other embodiments, the salt of Compound 1 has the structure

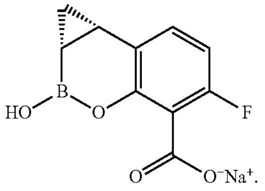

In some embodiments, the salt of Compound 1-a has the structure

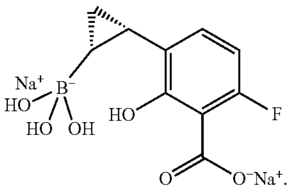

In other embodiments, the salt of Compound 1-a has the structure

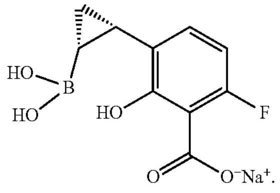

Methods of Preparation

Compound 1 and 1-a may be synthesized by method described in Example 1, by modification of this method, or using methods disclosed in International Patent Publication Nos. WO 2018/005662 and WO 2018/075084, the entireties of which is incorporated by reference herein. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Administration and Pharmaceutical Compositions

The combination of compound 1 or 1-a and additional medicament are administered at therapeutically effective dosages. In some embodiments, the additional medicament may be ceftolozane or sulbactam. In some embodiments, the additional medicament may be cefiderocol. While human dosage levels have yet to be optimized for the compounds and additional medicaments described herein, generally, a daily dose may be from about 0.25 mg/kg to about 120 mg/kg or more of body weight, from about 0.5 mg/kg or less to about 70 mg/kg, from about 1.0 mg/kg to about 50 mg/kg of body weight, or from about 1.5 mg/kg to about 10 mg/kg of body weight. Thus, for administration to a 70 kg person, the dosage range would be from about 17 mg per day to about 8000 mg per day, from about 35 mg per day or less to about 7000 mg per day or more, from about 70 mg per day to about 6000 mg per day, from about 100 mg per day to about 5000 mg per day, or from about 200 mg to about 3000 mg per day. The amount of active compound and additional medicament administered will, of course, be dependent on the subject and disease state being treated, the severity of the affliction, the manner and schedule of administration and the judgment of the prescribing physician.

Administration of the combination of Compound 1 or 1-a and additional medicament disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly.

The combination of Compound 1 or 1-a and additional medicaments useful as described herein can be formulated into pharmaceutical compositions for use in treatment of these conditions. In some embodiments, Compound 1 or 1-a and the additional medicament may be formulated in separate pharmaceutical compositions, whereas in other embodiments, Compound 1 or 1-a and the additional medicament may be formulated in the same pharmaceutical composition. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

Some embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound and additional medicament is basically determined by the way the compound and additional medicament is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

In some embodiments, Compound 1 or Compound 1-a and additional medicaments disclosed herein may be formulated into a single unit dosage form suitable for administering to a subject in need thereof. In other embodiments, Compound 1 or Compound 1-a and additional medicaments disclosed herein may be formulated into separate unit dosage forms.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Methods of Treatment

Some embodiments of the present invention include methods of treating bacterial infections with Compound 1 or 1a and an additional medicament and compositions comprising Compound 1 or 1a and an additional medicament described herein. Some embodiments include methods of treating bacterial infections with Compound 1 or 1a in combination with an additional medicament selected from the group consisting of sulbactam, ceftolozane, and cefiderocol. Some methods include administering the combination described herein to a subject in need thereof. In some embodiments, a subject can be an animal, e.g., a mammal (including a human). In some embodiments, the bacterial infection comprises a bacteria described herein. As will be appreciated from the foregoing, methods of treating a bacterial infection include methods for preventing bacterial infection in a subject at risk thereof.

In some embodiments, the subject is a human.

Some embodiments include co-administering Compound 1 or 1-a with the additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another such embodiment, administration in combination is accomplished by combining the agents in separate dosage forms. In another embodiment, the agents are administered sequentially. In one embodiment the agents are administered through the same route, such as orally or intravenously. In another embodiment, the agents are administered through different routes, such as one being administered orally and another being administered intravenous (i.v.).

In some embodiments, the additional medicament is selected from ceftolozane and sulbactam. In some embodiments, the additional medicament is cefiderocol.

Some specific embodiments include the combination of Compound 1, or a pharmaceutically acceptable salt thereof, with sulbactam. Other specific embodiments include the combination of Compound 1-a, or a pharmaceutically acceptable salt thereof, with sulbactam. Some specific embodiments include the combination of Compound 1, or a pharmaceutically acceptable salt thereof, with ceftolozane. Other specific embodiments include the combination of Compound 1-a, or a pharmaceutically acceptable salt thereof, with ceftolozane.

Some specific embodiments include the combination of Compound 1, or a pharmaceutically acceptable salt thereof, with cefiderocol. Other specific embodiments include the combination of Compound 1-a, or a pharmaceutically acceptable salt thereof, with cefiderocol.

The combination of Compound 1 or Compound 1-a and additional medicament may further included a second additional medicament. Examples of additional second medicaments include an antibacterial agent, antifungal agent, an antiviral agent, an anti-inflammatory agent and an anti-allergic agent. In some embodiments, the second additional medicaments include a β-lactam. Examples of such β-lactams include Amoxicillin, Ampicillin (e.g., Pivampicillin, Hetacillin, Bacampicillin, Methampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (e.g., Dicloxacillin, Flucloxacillin), Oxacillin, Methicillin, Nafcillin, Faropenem, Biapenem, Doripenem, Ertapenem, Imipenem, Meropenem, Panipenem, Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefiderocol, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, Ceftiofur, Cefquinome, Cefovecin, Aztreonam, Tigemonam and Carumonam.

Indications

The compounds and compositions comprising the compounds described herein can be used to treat bacterial infections. Bacterial infections that can be treated with the compounds, compositions and methods described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus.*

Some preferred embodiments are directed to treating infections comprising the bacteria *Acinetobacter baumannii*. Other preferred embodiments are directed to treating infections comprising the bacteria *Pseudomonas aeruginosa.*

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

Materials used in preparing the cyclic boronic acid ester derivative described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186, International Patent Publication No. WO 2009/064414, and International Patent Publication No. WO 2018/005662, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example is provided for the guidance of the reader, and represent preferred methods for making the compound exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

Example 1

Disodium Salt of 5-Fluoro-2-hydroxy-1a,7b-dihydro-1H-cyclopropa[c][1,2]benzoxaborinine-4-carboxylic acid (Compound 1')

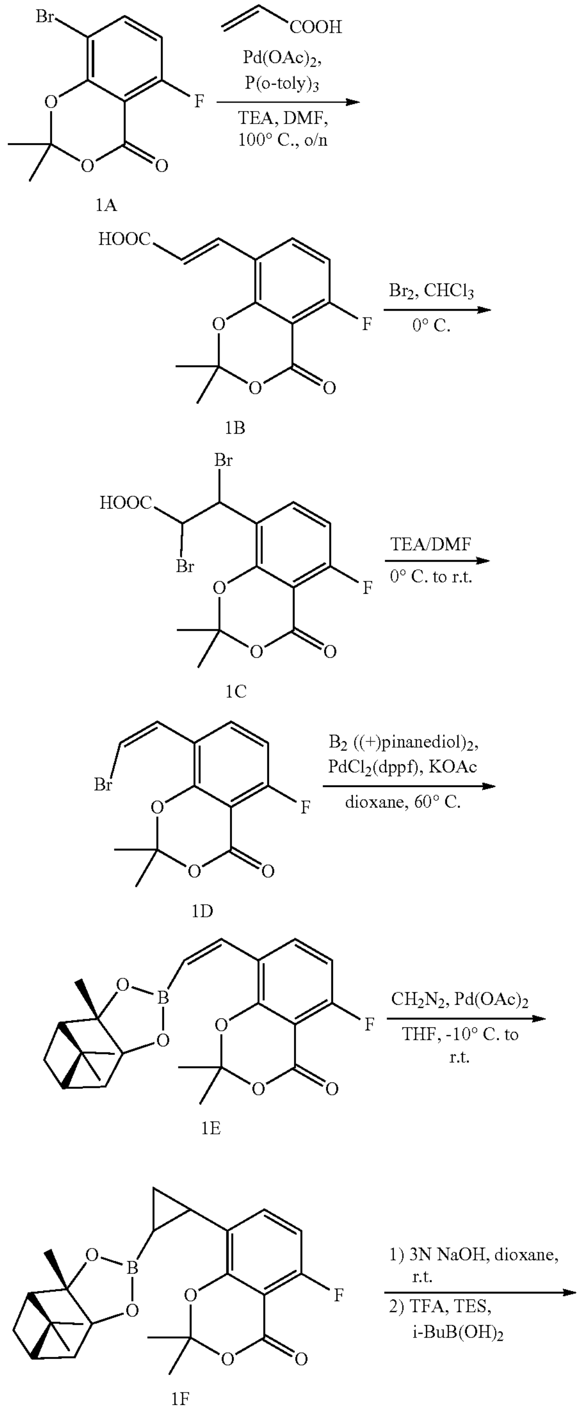

-continued

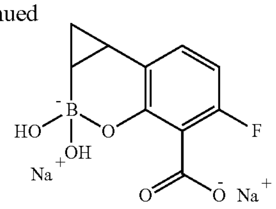

1'

Step 1: Synthesis of Compound 1A

Compound 1A was prepared from Boc-t-Butyl ester intermediate (previously disclosed in WO 2015/179308) by TFA deprotection followed by isopropylidene protection as described in step 2 of Example 1.

Step 2: Synthesis of Compound 1B

To the solution of compound 1A (16.0 g, 58 mmol, 1.0 eq) in DMF (50 mL) was added acrylic acid (6.0 mL, 87 mmol, 1.5 eq), TEA (24 mL, 175 mmol, 3 eq), $Pd(OAc)_2$ (651 mg, 2.9 mmol, 0.05 eq) and tri(o-tolyl)phosphine (1.77 g, 5.8 mmol, 0.1 eq). The reaction mixture was flushed with nitrogen and stirred at 100° C. for 14 hours. The reaction mixture was concentrated to dryness and the solid was washed with 0.2N HCl and DCM to give a yellow solid. The solid was re-crystallized in EtOAc and hexanes to give compound 1B (8.2 g, 53%) as an off-white solid. $^1H$ NMR ($CD_3OD$, 400 MHz): δ 8.01 (dd, 1H), 7.78 (d, J=16.4 Hz, 1H), 7.00 (dd, 1H), 6.57 (d, J=16.0 Hz, 1H), 1.80 (s, 6H).

Step 3: Synthesis of Compound 1C

To the suspension of compound 1B (8.2 g, 30.8 mmol, 1.0 eq) in chloroform (300 mL) was added bromine liquid (1.8 mL, 35.4 mmol, 1.15 eq) dropwise in 5 minutes at 0° C. The reaction solution was stirred at 0° C. for 2 hours before it was concentrated under reduced pressure. The obtained yellow solid is crude compound 1C (14.7 g), which was used directly for next step without purification.

Step 4: Synthesis of Compound 1D

To the solution of compound 1C (14.7 g, 30.8 mmol, 1.0 eq) in DMF (35 mL) was added triethylamine (8.6 mL, 61.6 mmol, 2.0 eq) dropwise in 2 minutes at 0° C. The resulting reaction mixture was slowly warmed up to rt and stirred for 8 hours. The reaction mixture was diluted with EtOAc and washed with 0.1N HCl and water. After dried over $Na_2SO_4$, the organic layer was concentrated and chromatography (hexanes/EtOAc=3/1 to 1/1) to give compound 4D (5.5 g) as an off-white solid. $^1H$ NMR ($CDCl_3$, 400 MHz): δ 8.20 (dd, 1H), 7.08 (d, J=8.0 Hz, 1H), 6.88 (t, J=8.2 Hz, 1H), 6.55 (d, J=8.0 Hz, 1H), 1.75 (s, 6H).

Step 5: Synthesis of Compound 1E

The mixture of compound 1D (700 mg, 2.3 mmol, 1.0 eq), bis((+)pinanediolato)diboron (1.24 g, 3.5 mmol, 1.5 eq), $PdCl_2$(dppf) (188 mg, 0.23 mmol, 0.1 eq) and KOAc (450 mg, 4.6 mmol, 2.0 eq) in dioxane (15 mL) was stirred at 60° C. for 2 hours under nitrogen atmosphere. The reaction mixture was diluted with EtOAc and washed with 0.1N HCl and water. After dried over $Na_2SO_4$, the organic layer was concentrated and purified by column chromatography (hexanes/EtOAc=3/1 to 1/1) to give compound 1E (240 mg, 26%) as a yellow solid. ESI-MS: $[M+H]^+$: 401.

Step 6: Synthesis of Compound 1F

To the solution of compound 1E (240 mg, 0.6 mmol, 1.0 eq) and $Pd(OAc)_2$ (6.8 mg, 0.03 mmol, 0.05 eq) in THF (3 mL) was slowly added diazomethane (6 mL, freshly made, about 0.2 to 0.3 M in ether) at −10° C. in 15 minutes. The solution was slowly warmed up to rt and stirred for 2 hours before it was concentrated to dryness. The obtained residue was and purified by column chromatography (hexanes/EtOAc=3/1 to 1/1) to give compound 1F (240 mg, 99%) as yellow oil. ESI-MS: $[M+H]^+$: 415.

Step 7: Synthesis of Compound 1'

The mixture of compound 1F (140 mg, 0.34 mmol, 1.0 eq) in dioxane (1.5 mL) and 3N NaOH (1.5 mL) was stirred at rt for 1 hour, LCMS indicating the disappearance of starting material. The reaction mixture was cooled to 0° C. and TES (250 mg), TFA (5 mL) and i-BuB$(OH)_2$ (100 mg) was added in sequence. The resulting yellow clear solution was stirred at rt for 2 hours before it was concentrated to dryness. The residue was dissolved in water/MeCN and purified by prep-HPLC (C18, acetonitrile and water as mobile phases, 0.1% TFA). The obtained solid (28 mg) was dissolved in MeCN/water and adjusted to pH=9.5 with IN NaOH (0.27 mL). After lyophilization, the crude sodium salt of Compound 1 was dissolved in 1.0 mL water and acetone (8.0 mL) was added dropwise. The resulting suspension was stirred at rt for 3 hours. The mixture was filtered and the solid was washed with 10% water in acetone twice to give Compound 1' (26 mg) as an off-white solid. $^1$H NMR ($D_2O$, 300 MHz): δ6.87 (t, J=7.2 Hz, 1H), 6.25 (d, J=8.4 Hz, 1H), 1.65-1.56 (m, 1H), 0.67-0.57 (m, 1H), 0.14-0.03 (m, 2H). F NMR ($D_2O$, 300 MHz): δ-124.9. ESI-MS: $[M-H_2O+H]^+$: 205.

Example 2

Embodiments of the present application are disclosed in further detail in the following example, which is not in any way intended to limit the scope of the present disclosure.

In this example the in vitro activity of Compound 1 was evaluated in combination with several β-lactams including sulbactam, meropenem, and ceftolozane against clinical isolates of carbapenem-resistant (CR) *Acinetobacter baumannii* (AB) and *Pseudomonas aeruginosa* (PA).

A total of 300 of carbapenem-resistant *Acinetobacter baumannii* (CRAB (including a subset of 100 CRAB strains containing defined carbapenemases and 1000 PA clinical isolates were tested by the reference broth microdilution method against β-lactams alone and combined with Compound 1 (4 μg/mL and 8 μg/mL). 500 PA isolates were selected to represent the normal distribution of meropenem (MER), ceftazidime-avibactam (CAZ-AVI), and ceftolozane-tazobactam (TOL-TAZ) resistance according to 2017 surveillance data (representative panel). Additionally, 652 PA isolates that were either non-susceptible (NS) to MER (Minimum Inhibitory Concentration (MIC), >2 μg/mL) or to TOL-TAZ (MIC, >4 μg/mL), or resistant (R) to CAZ-AVI (MIC, >8 μg/mL) (challenge panel) were also tested.

The activity data for Compound 1 in combination with sulbactam against representative AB strains are shown in Table 1. The data shows that the combination of Compound 1 with sulbactam improves the minimum inhibitory concentration of sulbactam alone against a variety of AB strains.

TABLE 1

Activity (Minimum Inhibitory Concentration (μg/mL)) of Compound 1 in Combination with Sulbactam (SUL) against Representative Strains

| Strain | Carbapenemase | SUL | SUL + Compound 1 at 4 μg/mL | SUL + Compound 1 at 8 μg/mL |
|---|---|---|---|---|
| AB1291 | KPC-2 | >64 | 0.25 | 0.05 |
| AB1358 | NDM-1 | >64 | 16 | 4 |
| AB1144 | NDM-1 | >64 | 4 | 0.25 |
| AB1359 | NDM-1 | >64 | 2 | ≤0.06 |
| AB1227 | OXA-23 | 64 | 8 | 8 |
| AB1244 | OXA-23 | 64 | 32 | 32 |
| AB1307 | OXA-23 | 32 | 4 | 2 |
| AB1333 | OXA-239 | 16 | 2 | 2 |
| AB1192 | OXA-24, OXA-72 | 32 | 4 | 4 |
| AB1223 | OXA-72 | 4 | 0.25 | ≤0.06 |

The minimum inhibitory concentration (MIC) distribution of various combinations of Compound 1 for the representative panel of PA is provided in Table 2. The combination of Compound 1 and ceftolozane has excellent potency against the representative panel of *P. aeruginosa* that reflects current MIC distributions. The combination of Compound 1 and ceftolozane is more potent than the combination of Compound 1 and meropenem, and more potent than the combinations of ceftolozane-tazobactam (TOL-TAZ) and ceftazidime-avibactam (CAZ-AVI) against this panel of isolates.

TABLE 2

Minimum Inhibitory Concentration Distributions of Compound 1 Combinations for the Representative Panel of PA (N = 500)

| MIC (μg/mL) | MER | MER + Compound 1 at 4 μg/mL | MER + Compound 1 at 8 μg/mL | TOL | TOL + TAZ | MER + Compound 1 at 4 μg/mL | TOL + Compound 1 at 8 μg/mL | CAZ + AVI |
|---|---|---|---|---|---|---|---|---|
| ≤0.06 | 4.8% | 9.0% | 10.8% | 0.2% | 0.0% | 0.6% | 2.4% | 0.2% |
| 0.125 | 14.2% | 26.0% | 29.0% | 0.2% | 0.2% | 2.6% | 3.4% | 0.2% |
| 0.25 | 33.0% | 47.8% | 50.8% | 2.8% | 3.6% | 8.0% | 13.2% | 0.8% |
| 0.5 | 51.0% | 61.0% | 62.6% | 56.2% | 55.8% | 66.0% | 69.6% | 4.0% |
| 1 | 66.2% | 70.6% | 71.6% | 77.4% | 80.6% | 89.2% | 91.2% | 28.4% |
| 2 | 73.2% | 82.0% | 82.8% | 85.2% | 88.6% | 93.8% | 96.4% | 66.8% |
| 4 | 79.8% | 85.8% | 86.4% | 90.4% | 91.8% | 95.6% | 97.6% | 82.4% |
| 8 | 84.8% | 91.0% | 91.6% | 92.2% | 93.8% | 97.4% | 97.8% | 92.2% |
| 16 | 90.4% | 95.8% | 96.2% | 93.0% | 93.8% | 98.2% | 98.2% | 94.8% |

TABLE 2-continued

| Minimum Inhibitory Concentration Distributions of Compound 1 Combinations for the Representative Panel of PA (N = 500) | | | | | | | | |
|---|---|---|---|---|---|---|---|---|
| MIC (µg/mL) | MER | MER + Compound 1 at 4 µg/mL | MER + Compound 1 at 8 µg/mL | TOL | TOL + TAZ | MER + Compound 1 at 4 µg/mL | TOL + Compound 1 at 8 µg/mL | CAZ + AVI |
| 32 | 95.4% | 98.0% | 98.2% | 93.2% | 99.8% | 98.4% | 98.4% | 97.0% |
| >32 | 100.0% | 100.0% | 100.0% | 100.0% | 100.0% | 100.0% | 100.0% | 100.0% |

MER, meropenem;
TOL, ceftolozane;
SUL, sulbactam;
CAZ, ceftazidime;
AVI, avibactam,
TAZ, tazobactam.
AVI and TAZ at 4 µg/mL The MIC distribution of combinations of Compound 1 with various antibiotics for the challenge panel of *Pseudomonas aeruginosa* is provided in Table 3. The data shows that the combination of Compound 1 with ceftolozane have increased potency against the challenge panel of PA. The combination of Compound 1 with ceftolozane is more potent than the combination of Compound 1 with meropenem, and more potent than the combinations of ceftolozane-tazobactam (TOL-TAZ) and ceftazidime-avibactam (CAZ-AVI) against the challenge panel of PA enriched in ceftazidime-avibactam resistant and meropenem, caftolozane-tazobactam non-susceptible isolates.

TABLE 3

| MIC Distributions of Compound 1 (C1) Combinations for the Representative Panel of PA (N = 500) | | | | | | | | |
|---|---|---|---|---|---|---|---|---|
| | MER NS (MER >2 µg/mL), N = 612 | | | | | CAZ-AVI R (CAZ-AVI >8 µg/mL) | | |
| MIC (µg/mL) | MER | MER + C1 | TOL + TAZ | TOL + C1 | CAZ + AVI | MER | MER + C1 | TOL + TAZ |
| ≥0.06 | 0.0% | 1.3% | 12.4% | 0.5% | 0.0% | .3% | 1.6% | 26.0% |
| 0.125 | 0.0% | 1.6% | 12.4% | 0.7% | 0.0% | .3% | 3.2% | 26.0% |
| 0.25 | .0% | 2.1% | 12.6% | 2.0% | 0.0% | .6% | 5.2% | 26.0% |
| 0.5 | .0% | 4.6% | 20.6% | 18.5% | 0.2% | .2% | 8.8% | 26.3% |
| 1 | .0% | 7.0% | 39.1% | 52.3% | 2.8% | .5% | 12.0% | 26.9% |
| 2 | .0% | 26.5% | 48.2% | 72.1% | 14.4% | .8% | 19.8% | 28.9% |
| 4 | .5% | 41.3% | 55.4% | 83.8% | 36.1% | 1.0% | 33.8% | 36.4% |
| 8 | 7.5% | 63.9% | 63.1% | 87.4% | 53.6% | 8.2% | 6.2% | 4.8% |
| 16 | 6.7% | 83.2% | 8.3% | 89.7% | 66.5% | 8.9% | 3.1% | 8.7% |
| 32 | 0.4% | 92.2% | 5.1% | 91.0% | 82.0% | 3.2% | 5.7% | 0.3% |
| >32 | 100.0% | 100.0% | 00.0% | 100.0% | 100.0% | 100.0% | 100.0% | 100.0% |

| | CAZ-AVI R (CAZ-AVI >8 µg/mL) | | TOL-TAZ NS (TOL-TAZ >4 µg/mL) | | | | |
|---|---|---|---|---|---|---|---|
| MIC (µg/mL) | TOL + C1 | CAZ + AVI | MER | MER + C1 | TOL + TAZ | TOL + C1 | CAZ + AVI |
| ≥0.06 | 0.3% | 0.0% | 0.3% | 3.0% | 0.0% | 1.3% | 0.0% |
| 0.125 | 0.6% | 0.0% | 1.3% | 5.0% | 0.0% | 1.3% | 0.0% |
| 0.25 | 0.6% | 0.0% | 2.7% | 8.7% | 0.0% | 2.3% | 0.3% |
| 0.5 | 3.2% | 0.0% | 3.7% | 13.4% | 0.0% | 9.4% | 0.3% |
| 1 | 21.8% | 0.0% | 6.0% | 16.7% | 0.0% | 33.1% | 1.0% |
| 2 | 45.5% | 0.0% | 8.7% | 35.5% | 0.0% | 55.9% | 6.0% |
| 4 | 67.2% | 0.0% | 13.7% | 49.8% | 0.0% | 72.9% | 21.7% |
| 8 | 74.7% | 0.0% | 22.1% | 70.6% | 20.4% | 78.6% | 34.4% |
| 16 | 79.2% | 29.9% | 32.8% | 83.9% | 32.1% | 82.6% | 47.2% |
| 32 | 82.5% | 62.7% | 58.2% | 90.0% | 89.3% | 85.3% | 70.6% |
| >32 | 100.0% | 100.0% | 100.0% | 100.0% | 100.0% | 100.0% | 100.0% |

Compound 1 at 8 µg/mL;
AVI and TAZ at 4 µg/mL

The activity of Compound 1 combinations with meropenem (MER), ceftolozane (TOL), and sulbactam (SUL) is shown in Table 4. Combinations of Compound 1 with various β-lactam antibiotics displayed potent activity against CRAB and PA isolates as shown in Table 4 and FIGS. 1A and 1B. The combination of Compound 1 with TOL exhibited activity against 300 CRAB, including 100 CRAB with defined CPs as well as against representative and challenge PA strains and restored susceptibility (S) to TOL. TOL-Compound 1 was also more potent compared to TOL-TAZ and CAZ-AVI against TOL-TAZ- and CAZ-AVI-resistant isolates.

TABLE 4

Activity of Combinations of Compound 1 with various β-lactam antibiotics

| Organisms (no.) | MER | MER + Compound 1 | TOL | TOL + Compound 1 | SUL | SUL + Compound 1 |
|---|---|---|---|---|---|---|
| | MIC$_{50}$/MIC$_{90}$ (μg/mL) (% susceptible, [S]) | | | | | |
| CRAB (300) | >32/>32 (1.0) | 2/8 (97.0) | >32/>32 (1.3) | 16/32 (13.7) | ND | ND |
| AB CP (100) | >32/>32 (0.0) | 4/8 (96.0) | >32/>32 (0.0) | 16/32 (12) | >32/>32 | 8/16 |

| | MER | MER + Compound 1 | TOL | TOL + Compound 1 | TOL + TAZ | CAZ-AVI |
|---|---|---|---|---|---|---|
| PA (Representative, 500) | 0.5/16 (84.8) | 0.5/8 (85.8) | 0.5/4 (90.4) | 0.5/2 (95.6) | 0.5/4 (91.8) | 2/8 (92.2) |
| PA (Challenge, 652)) | 16/>32 (31.9) | 8/32 (60.7) | 16/>32 (44.0) | 2/32 (75) | 4/32 (54) | 8/>32 (52.8) |
| PA (MER MIC >2) (612) | 32/>32 (27.5) | 8/>32 (58.2) | 4/>32 (56.2) | 2/>32 (74.5) | 4/>32 (55.4) | 8/>32 (53.6) |
| PA (TOL-TAZ MIC >4) (39) | 32/>32 (21.1) | 8/>32 (64.2) | >32/>32 (3.3) | 8/>32 (58.2) | >32/>32 (0.0) | 32/>32 (34.4) |
| PA (CAZ-AVI MIC >8) (37) | 32/>32 (18.9) | 16/>32 (49.0) | >32/>32 (18.2) | 8/>32 (49.0) | 32/32 (36.4) | >32/>32 (0.0) |

MER, meropenem;
TOL, ceftolozane;
SUL, sulbactam;
CAZ, ceftazidime;
AVI, avibactam.
Compound 1, AVI, and TAZ were tested at fixed 4 μg/mL.
Breakpoints:
MER ≤8 μg/mL;
TOL ≤4 μg/mL:
CAZ ≤8 μg/mL.

In addition, 509 Carbapenem-Resistant *Enterobacteriaceae* were tested with meropenem, cefepime, and ceftolozane alone and in combination with Compound 1 at 8 μg/mL. Furthermore, 262 strains of *P. aeruginosa* with a meropenem MIC>2 μg/mL were tested with meropenem, ceftolozane, cefepime and piperacillin alone and in combination with Compound 1 at 8 μg/mL.

Figure 2:
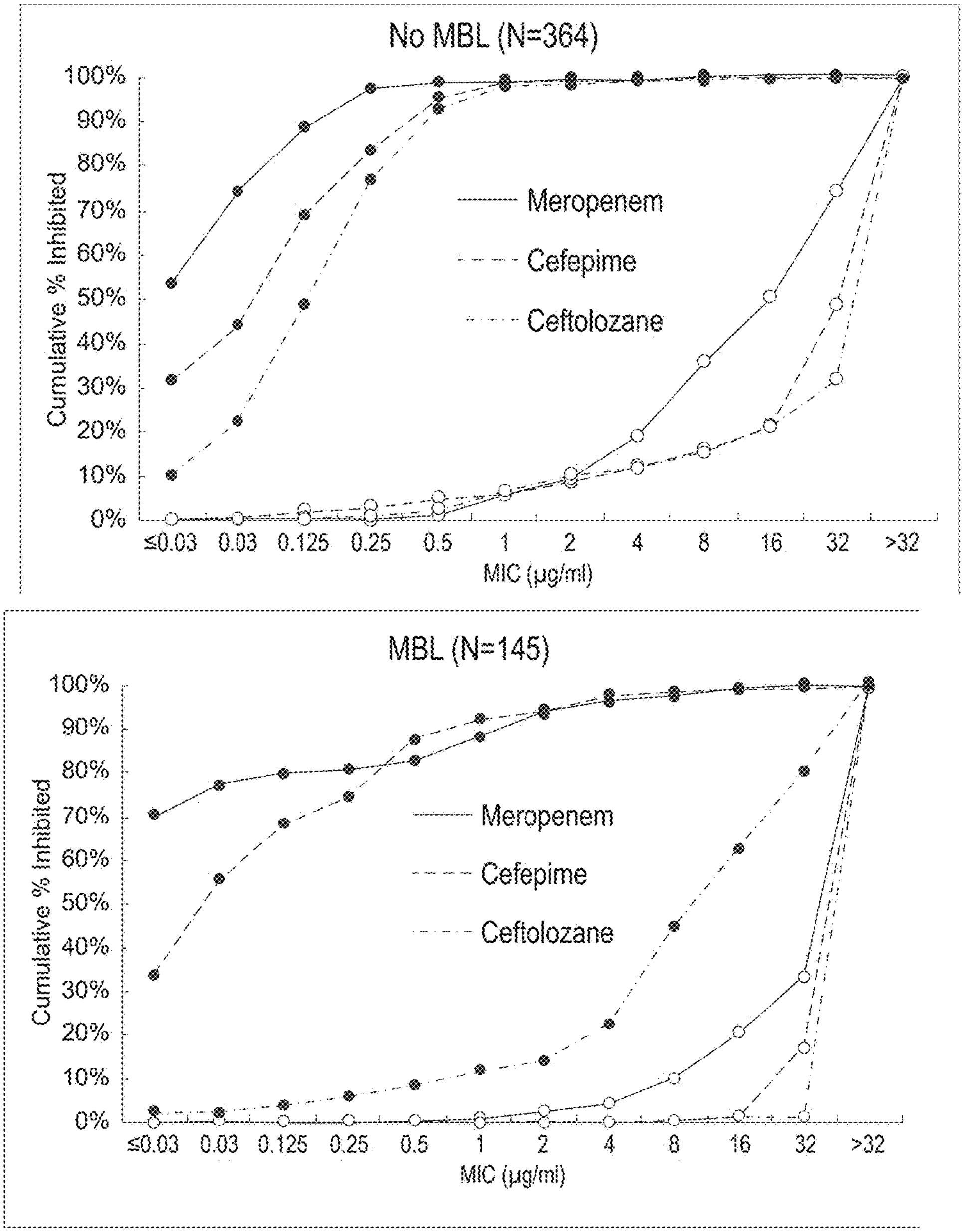
FIG. 2 shows the minimum inhibitory concentration distribution of meropenem, cefepime and ceftolozane alone and with Compound 1 at 8 μg/mL for Carbapenem-Resistant *Enterobacteriaceae*. The Figure shows data for Carbapenem-Resistant *Enterobacteriaceae* lacking metallo-β-lactamases (No MBL; N=264) and having metallo-β-lactamases (MBL; N=145).

The MIC distribution of combinations of Compound 1 with meropenem, cefepime and cetolozane alone, or with Compound 1 at 8 μg/mL for Carbapenem-Resistant Enterobacteriaceae were tested. Compound 1 significantly increased potency of all tested antibiotics and restores the petency of meropenem, cefepime, and ceftolozane against Carbapenem-Resistant Enterobacteriaceae (FIG. 2).

Compound 1 also increased the proportion of susceptible *P. aeruginosa.* 262 strains of *P. aeruginosa* having a meropenem MIC greater than 2 μg/mL were tested with meropenem, ceftolozane, cefepime and piperacillin alone and Compound 1 at 8 μg/mL. Table 5 shows changes in % of susceptible organisms at breakpoints. Compound 1 increased the proportion of susceptible organisms for all tested agents.

TABLE 5

Susceptibility Testing of *P. aeruginosa* with meropenem (MER), ceftolozane (TOL), cefepime (FEP) and piperacillin (PP) alone and Compound 1 at 8 μg/mL

| | MER | MER + Compound 1 | TOL + TAZ | TOL + Compound 1 | FEP | FEP + Compound 1 | PIP + TAZ | PIP + Compound 1 |
|---|---|---|---|---|---|---|---|---|
| All strains (N = 262) | 42 | 66 | 49 | 77 | 20 | 65 | 17 | 76 |
| No MBL (N = 206) | 51 | 75 | 61 | 92 | 24 | 76 | 19 | 80 |
| MBL (N = 56) | 7 | 30 | 5 | 23 | 4 | 23 | 7 | 61 |

Breakpoints:
≤8 μg/mL for meropenem and cefepime;
≤4 μg/mL for ceftolozane;
≤16 μg/mL for piperacillin;
MBL (metallo-β-lactamase)

Example 3

Embodiments of the present application are disclosed in further detail in the following example, which is not in any way intended to limit the scope of the present disclosure.

In this example, the antibiotics meropenem, cefepime, ceftolozane and cefiderocol, were tested in combination with Compound 1 at 4 μg/ml and 8 μg/ml against a panel of 510 clinical isolates representing various types of carbapenem resistant Enterobacteriaceae (CRE). Cefiderocol was tested at standard conditions, in iron proficient media. MIC90 of all tested antibiotics against this panel were in resistant range and Compound 1 shifted MIC90 of all antibiotics (except ceftolozane tested against metallo beta-lactamases, MBL) into susceptible range. The results are presented in Table 6 and show that Compound 1 significantly enhances the potency of these antibiotics against carbapenem resistant Enterobacteriaceae

TABLE 6

Activity of Compound 1 in combination with meropenem (MER), cefepime (FEP), ceftolozane (TOL) and cefiderocol (DER) against various types of CRE (N = 510)

| | MER | MER w/QPX at 4 μg/ml | MER w/QPX at 8 μg/ml | FEP | FEP w/QPX at 4 μg/ml | FEP w/QPX at 8 μg/ml | TOL | TOL w/QPX at 4 μg/ml | TOL w/QPX at 8 μg/ml | DER | DER w/QPX at 4 μg/ml | DER w/QPX at 8 μg/ml |
|---|---|---|---|---|---|---|---|---|---|---|---|---|
| KPC, N = 168 | | | | | | | | | | | | |
| MIC50 | 32 | <=0.06 | <=0.06 | 32 | 0.125 | 0.06 | >32 | 0.25 | 0.125 | 2 | 0.125 | 0.06 |
| MIC90 | >32 | 0.25 | 0.125 | >32 | 0.5 | 0.25 | >32 | 1 | 0.5 | 32 | 2 | 1 |
| OXA, N = 152 | | | | | | | | | | | | |
| MIC50 | 32 | 0.06 | <=0.06 | >32 | 0.25 | 0.125 | >32 | 0.5 | 0.25 | 1 | 0.125 | 0.06 |
| MIC90 | >32 | 0.125 | 0.125 | >32 | 0.5 | 0.5 | >32 | 1 | 0.5 | 8 | 0.5 | 0.5 |
| non-carbapenemase producing CRE, N = 45 | | | | | | | | | | | | |
| MIC50 | 8 | 0.25 | 0.125 | >32 | 0.5 | 0.125 | >32 | 0.5 | 0.25 | 2 | 0.5 | 0.25 |
| MIC90 | 16 | 2 | 0.5 | >32 | 2 | 1 | >32 | 8 | 1 | 32 | 4 | 2 |
| MBL, N = 145 | | | | | | | | | | | | |
| MIC50 | >32 | 0.06 | <=0.06 | >32 | 0.25 | 0.06 | >32 | >32 | 16 | 8 | 0.125 | 0.06 |
| MIC90 | >32 | 8 | 2 | >32 | 8 | 1 | >32 | >32 | >32 | >32 | 1 | 0.5 |

MER = meropenem;
FEP = cefepime;
TOL - ceftolozane;
DER = cefiderocol;
QPX = Compound 1

Example 4

Embodiments of the present application are disclosed in further detail in the following example, which is not in any way intended to limit the scope of the present disclosure.

In another experiment, various antibiotics, meropenem, cefepime, ceftolozane and cefiderocol, were tested in combination with Compound 1 at 4 μg/ml and 8 μg/ml against the panel of 503 clinical isolates of carbapenem resistant *Acinetobacter baumannii*. Compound 1 significantly enhances the potency of meropenem and cefiderocol against this panel of highly resistant strains shifting MIC90 of both antibiotics into susceptible level. Cefiderocol was tested at standard conditions, in iron proficient media. The results are presented in Table 7.

TABLE 7

Activity of Compound 1 in combination with various antibiotics against carbapenem resistant *Acinetobacter baumannii* (N = 503)

| | MER | MER-QPX at 4 μg/ml | MER-QPX at 8 μg/ml | FEP | FEP-QPX at 4 μg/ml | FEP-QPX at 8 μg/ml | TOL | TOL-QPX at 4 μg/ml | TOL-QPX at 8 μg/ml | DER | DER-QPX at 4 μg/ml | DER-QPX at 8 μg/ml |
|---|---|---|---|---|---|---|---|---|---|---|---|---|
| $MIC_{50}$ | >32 | 1 | 0.5 | >32 | 16 | 16 | >32 | 16 | 8 | 1 | 0.5 | 0.5 |
| $MIC_{90}$ | >32 | 8 | 4 | >32 | >32 | 32 | >32 | 32 | 32 | 32 | 2 | 2 |

Although the present disclosure has been described with reference to embodiments and examples, it should be understood that numerous and various modifications can be made without departing from the spirit of the present disclosure. Accordingly, the present disclosure is limited only by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

What is claimed is:

1. A method of treating a bacterial infection in a subject in need thereof, comprising administering a pharmaceutical composition comprising a therapeutically effect amount of cefiderocol or a pharmaceutically acceptable salt thereof and a therapeutically effective amount of a compound having the structure:

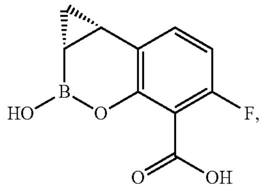

or a pharmaceutically acceptable salt thereof, and a pharmaceutically acceptable excipient to the subject;

wherein the bacterial infection comprises a bacteria selected from the group consisting of *Pseudomonas aeruginosa, Acinetobacter baumannii*, and Enterobacteriaceae.

2. The method of claim 1, wherein the infection comprises the bacteria *Pseudomonas aeruginosa.*

3. The method of claim 1, wherein the infection comprises the bacteria *Acinetobacter baumannii.*

4. A method of treating a bacterial infection in a subject in need thereof, comprising administering to the subject a therapeutically effect amount of a compound having the structure:

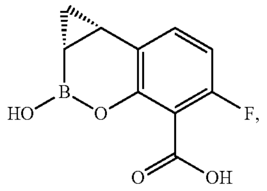 [SMILES: O=C(O)c1c(F)ccc2c1OB(O)[C@@H]1C[C@H]21]

or a pharmaceutically acceptable salt thereof, and a therapeutically effect amount of an additional medicament, wherein the additional medicament is cefiderocol or a pharmaceutically acceptable salt thereof;

wherein the bacterial infection comprises a bacteria selected from the group consisting of *Pseudomonas aeruginosa, Acinetobacter baumannii*, and Enterobacteriaceae.

5. The method of claim 4, wherein the pharmaceutically acceptable salt is an alkaline metal salt or an ammonium salt.

6. The method of claim 5, wherein the pharmaceutically acceptable salt is a sodium salt.

7. The method of claim 6, wherein the sodium salt is

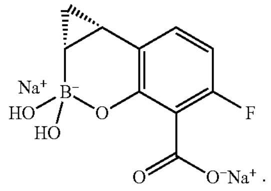

8. The method of claim 6, wherein the sodium salt is

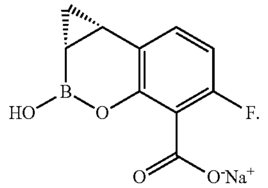

9. The method of claim 4, wherein the compound and additional medicament are administered simultaneously.

10. The method claim 4, wherein the compound and additional medicament are administered sequentially.

11. The method of claim 4, wherein the infection comprises the bacteria *Pseudomonas aeruginosa* or *Acinetobacter baumannii.*

12. The method of claim 1, wherein the pharmaceutically acceptable salt is an alkaline metal salt or an ammonium salt.

13. The method of claim 12, wherein the pharmaceutically acceptable salt is a sodium salt.

14. The method of claim 13, wherein the sodium salt is

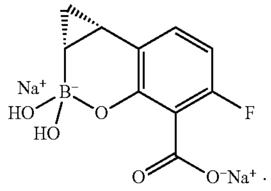

15. The method of claim 13, wherein the sodium salt is

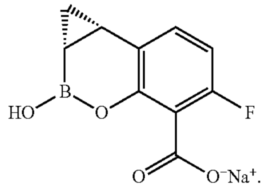

16. The method of claim 1, wherein the compound is

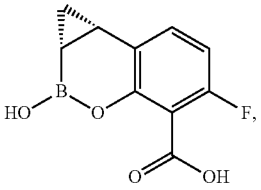 [SMILES: O=C(O)c1c(F)ccc2c1OB(O)[C@@H]1C[C@H]21]

or a pharmaceutically acceptable salt thereof.

17. The method of claim 16, wherein the compound is

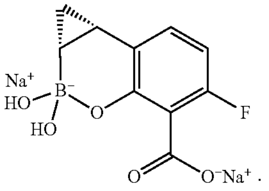

18. The method of claim 4, wherein the compound is

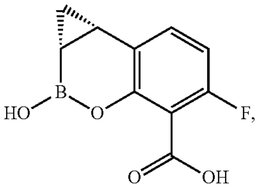 [SMILES: O=C(O)c1c(F)ccc2c1OB(O)[C@@H]1C[C@H]21]

or a pharmaceutically acceptable salt thereof.

19. The method of claim 18, wherein the compound is

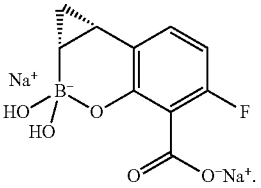

20. The method of claim 4, wherein the infection comprises the bacteria *Pseudomonas aeruginosa.*

21. The method of claim 4, wherein the infection comprises the bacteria *Acinetobacter baumannii.*

22. The method of claim 4, wherein the infection comprises the bacteria Enterobacteriaceae.

* * * * *